(12) United States Patent
Hewitson et al.

(10) Patent No.: US 9,857,339 B2
(45) Date of Patent: Jan. 2, 2018

(54) AUTOMATED SAMPLING AND REACTION SYSTEM FOR HIGH PRESSURE LIQUID CHROMATOGRAPHY AND OTHER TYPES OF DETECTION

(71) Applicant: Waters Technologies Corporation, Milford, MA (US)

(72) Inventors: Hillary B Hewitson, Sharon, MA (US); Sylvain G Cormier, Mendon, MA (US); Charles H. Phoebe, Jr., Uxbridge, MA (US); Aaron D Phoebe, Uxbridge, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/979,066

(22) Filed: Dec. 22, 2015

(65) Prior Publication Data
US 2016/0195564 A1 Jul. 7, 2016

Related U.S. Application Data

(60) Provisional application No. 62/100,252, filed on Jan. 6, 2015.

(51) Int. Cl.
*G01N 30/20* (2006.01)
*G01N 30/06* (2006.01)
(Continued)

(52) U.S. Cl.
CPC ............. *G01N 30/20* (2013.01); *G01N 30/06* (2013.01); *G01N 30/24* (2013.01);
(Continued)

(58) Field of Classification Search
CPC ....................................................... B01L 10/00
(Continued)

(56) References Cited

U.S. PATENT DOCUMENTS 3,744,219 A * 7/1973 Tindle et al. ................... 96/103
3,757,583 A * 9/1973 Ludewig, Jr. .............. 73/863.33
(Continued)

OTHER PUBLICATIONS

Jensen, K. F. et al., Tools of Chemical Synthesis in Microsystems, The Royal Society of Chemistry, May 28, 2014.
(Continued)

*Primary Examiner* — Brian J Sines
(74) *Attorney, Agent, or Firm* — Schmeiser, Olsen & Watts LLP

(57) ABSTRACT

Automated sampling and reaction systems and methods of using the same are provided. The automated sampling and reaction system has a microreactor in fluidic communication with an external sampling valve. The external sampling valve is connected to a priming valve and can be configured to draw sample from a reactor or a reactor stream. The microreactor is connected to a reagent valve and an injection valve. The reagent valve can be configured to draw reagent from a reagent reservoir and discharge reagent to the microreactor to react with sample. The priming valve can be configured to draw wash from a wash reservoir and discharge wash to the external sampling valve to move sample from the external sampling valve to the microreactor. The injection valve is in fluidic communication with a column or detector and discharges the secondary sample into a solvent composition stream.

13 Claims, 13 Drawing Sheets

(51) Int. Cl.
*G01N 30/24* (2006.01)
*G01N 35/10* (2006.01)
*G01N 35/00* (2006.01)

(52) U.S. Cl.
CPC ... *G01N 35/1097* (2013.01); *G01N 2030/067* (2013.01); *G01N 2030/207* (2013.01); *G01N 2035/00514* (2013.01); *G01N 2035/1032* (2013.01)

(58) Field of Classification Search
USPC .................... 422/81, 502, 503, 537, 129
See application file for complete search history.

(56) References Cited

U.S. PATENT DOCUMENTS

| | | | | |
|---|---|---|---|---|
| 3,827,302 | A | * | 8/1974 | Sato ............................ 73/863.33 |
| 3,918,913 | A | * | 11/1975 | Stevenson et al. ........ 73/863.72 |
| 4,837,157 | A | | 6/1989 | Turnell et al. |
| 8,343,774 | B2 | | 1/2013 | Cormier |
| 2002/0011437 | A1 | | 1/2002 | Kaito et al. |
| 2007/0062875 | A1 | * | 3/2007 | Usowicz et al. ............... 210/659 |
| 2007/0277596 | A1 | * | 12/2007 | Kim et al. ................... 73/61.48 |
| 2008/0286170 | A1 | * | 11/2008 | Diamond et al. ............. 422/188 |
| 2011/0016955 | A1 | | 1/2011 | Cormier |
| 2011/0020939 | A1 | * | 1/2011 | Cormier ............................ 436/8 |
| 2012/0103075 | A1 | | 5/2012 | Cormier et al. |
| 2012/0305464 | A1 | | 12/2012 | Cormier |
| 2014/0179011 | A1 | | 6/2014 | Brousmiche et al. |

OTHER PUBLICATIONS

Erfeld Mikortechnik BTS, Product Catalog, Retrieved on Jun. 9, 2014.
Micronit Microfluidics, Microfluidic Research Products, Retrieved on Jun. 9, 2014.
Mikroglas, Microreaction Technology, Retrieved on Jun. 9, 2014.
Vizza, A. et al., Coming Advanced-Flow Reactor Technologies: from Lab to Production a Seamless Scale-up, Corning Incorporated, 2013.
Pissavini, S. et al., Corning Advance Flow Reactor Tool for Laboratory, Process Development and Production, CPAC Rome, Mar. 2011.
Majors, R. R., Sample Preparation Fundamentals for Chromatography, Agilent Technologies, Inc., Nov. 13, 2013.
Lionix, Microfluidics, www.lionixbv.nl/technology/technology-microfluidics.html, Retrieved on Jun. 9, 2014.
Syrris, Asia Mircoreactors, syrris.com/flow-products/asia-modules/asia-microreactors, Retrieved on Jun. 9, 2014.
Micronit Microfluidics, Fluidic Connecto Pro, www.micronit.com/wp-content/uploads/2014/07/Fluidic-Connect-PRO1.pdf, Retrieved on Jun. 9, 2014.
Syrris, Asia Sampler and Dilutor, syrris.com/flow-products/asia-modules/asia-sampler-and-dilutor, Retrieved on Jun. 9, 2014.
European Search Report, 16150281.0, dated Jun. 7, 2016.

* cited by examiner

AUTOMATED SAMPLING AND REACTION SYSTEM FOR HIGH PRESSURE LIQUID CHROMATOGRAPHY AND OTHER TYPES OF DETECTION

CROSS REFERENCE TO RELATED APPLICATIONS

This application claims the benefit of priority to the U.S. Provisional Application No. 62/100,252 filed Jan. 6, 2015 incorporated herein by reference.

BACKGROUND OF THE INVENTION

Most manufacturing industries use chromatography and other types of separation and detection systems to evaluate the process reactions or manufacturing process lines. For example, pharmaceutical manufacturers often use a chromatography system to monitor their process line by taking samples at various times or at different points along the process line to ensure that a manufacturing batch is to specification. Samples may include complex mixtures of proteins, protein precursors, protein fragments, reaction products, and other compounds, to list but a few. Other manufacturers may use their chromatography systems to profile a certain biochemical reaction, taking samples from the same point in the process line over time as the reaction progresses.

For every industry, preservation and transport of sample presents a particular challenge as it is imperative that sample represents the batch or flow stream that is being tested or otherwise investigated. During transport, changes in and to the physical and chemical makeup of the collected sample must be avoided for the measurements to be reliable. For example, the degradation of the sample due to environmental stress (i.e., heat, cold, oxygen) can cause an erroneous result. Furthermore, any sample preparation prior to the measurement should be performed with a minimum loss of sample and without unwanted modifications and avoiding the additional of extraneous impurities.

The manner of acquiring samples for analysis can be manually intensive. Typically, an individual draws sample from a process line, reactor, reactor stream or the like. He or she then carries it to the separation and detection system and loads it into the system for injection and analysis. Throughout this handling, care must be taken to label the sample properly and to ensure a well-documented chain of custody, or otherwise risk introducing uncertainty into the results.

If a sample needs to be converted to a form suitable for the measurement step, sample preparations such as filtration, quenching, dilution, or derivatization are made before sample injection into a liquid chromatography system. In this case, the sample preparation apparatus must be thoroughly washed to avoid contamination with the previous sample. Manual sample preparations can be wasteful and cost ineffective as larger amounts of the sample need to be taken. Manual sample preparation introduces the risk of irreproducible results and affords sources of error to be generated during sample analysis.

For example, manual sample preparation for chemical derivatization prior to the injection is very time consuming. After manually acquiring the sample, the individual must next thoroughly mix the sample with a reagent, or multiple reagents. Then, the individual must apply for example heat to the container within which the derivatization occurs, ensuring that the heat is applied evenly throughout the container for a specified time, sometimes hours, in order for the chemical reaction to go to completion. Each pre-analysis step can influence the overall accuracy and reliability of the results. In some cases, variations in the pre-analysis steps can introduce errors in the results that are greater in magnitude than the properties of the sample that are being measured.

SUMMARY OF THE INVENTION

Systems, methods and devices for automated sample preparation and sample reaction are provided herein. One aspect provides an automated sampling and reaction system including an external sampling valve, a microreactor in fluid communication with the external sampling valve, and an injection valve connected to the microreactor. In exemplary embodiments, the external sampling valve can be connected to a priming valve. The external sampling valve can be configured to draw sample from a reactor or a reactor stream. The priming valve can be configured to discharge wash to the external sampling valve. For example, the priming valve can be configured to draw wash from a wash reservoir. The microreactor can be connected to a reagent valve. For example, the reagent valve can be configured to draw reagent from a reagent reservoir or to discharge reagent into the microreactor. In some exemplary embodiments, the reagent valve can be configured to discharge reagent to the microreactor and the external sampling valve can be configured to discharge sample to the microreactor to form a secondary sample. The microreactor, for example, can be a chip, capillary, micro-structured or industrial type microreactor. In some embodiments, the injection valve can be configured to discharge the secondary sample into a solvent composition stream. In other aspects, a liquid chromatography system can include the automated sampling and reaction system.

In some embodiments, the automated sampling and reaction system can include a mixing tee connected to the external sampling valve and the microreactor. In further embodiments, a diluent valve can be connected to the mixing tee. For example, the diluent valve can be configured to draw diluent from a diluent reservoir. Also, the diluent valve can be configured to discharge diluent to the mixing tee.

In a first configuration, the external sampling valve draws a discrete amount of sample or continuous sample from a reactor or reactor flow stream. In a second configuration, the external sampling valve discharges drawn sample via a backwash discharged from the sample pump to the mixing tee. In exemplary embodiments, the automated sampling and reaction system can operate under a pressure greater than about 1 atmosphere or can be configured to draw from a non-pressurized source. When drawing from a non-pressurized source, the system can include at least one external auxiliary sampling valve and at least one external sample pump. For example, the external auxiliary sample valve can be connected to the external sample pump, the external sampling valve and to the reactor or reactor stream. In some embodiments, the automated sampling and reaction system can have a selection valve that is connected to the external auxiliary sampling valve and to the external sampling valve. The selection valve can be connected to a plurality of the external sampling valves.

In some embodiments, the automated sampling and reaction system can include a pumping system having one or more pumps working in combination with the priming valve, the diluent valve and/or the reagent valve. For example, the pumping system can have one or more pumps working in combination with the priming valve and the reagent valve. In exemplary embodiments, the diluent pump can be configured to draw diluent from the diluent reservoir and discharge diluent to the mixing tee.

In another aspect, methods of quantitative analysis of a liquid solution are provided. An exemplary embodiment of such methods includes the steps of selecting a source of sample from a reactor or a reactor flow stream, acquiring sample from the reactor or the reactor flow stream through an external sampling valve, drawing wash through a priming valve in fluidic communication with the external sampling valve, reacting sample with a reagent discharged from a reagent valve into a microreactor, discharging the secondary sample into a second sample loop of an injection valve, and injecting sample from the injection valve into a solvent composition stream in fluidic communication with a column or detector. For example, the external sampling valve can be configured to draw sample into a first sample loop. In exemplary embodiments, the microreactor can be in fluidic communication with the external sampling valve. The reagent valve can be connected to the microreactor. In the microreactor, a secondary sample can be formed. In exemplary embodiments, the priming valve can be configured to discharge wash from the second sample loop to the external sampling valve.

In some embodiments, the sample can be acquired from the reactor or the reactor flow stream operating at pressure of more than one atmosphere. In some embodiments, sample can be acquired from the reactor or the reactor flow stream operating at a pressure of one atmosphere or less. For example, sample can be acquired by an external sample pump connected to an external auxiliary sampling valve. The external pump then discharges drawn sample via a backwash provided by a sample pump to a mixing tee connected to the microreactor. In further embodiments, the method can include the step of quenching sample at the mixing tee. In some embodiments, the reagent can be an MS active, fluorescent rapid tagging reagent and the secondary sample can be an MS active, fluorescent biomolecule.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
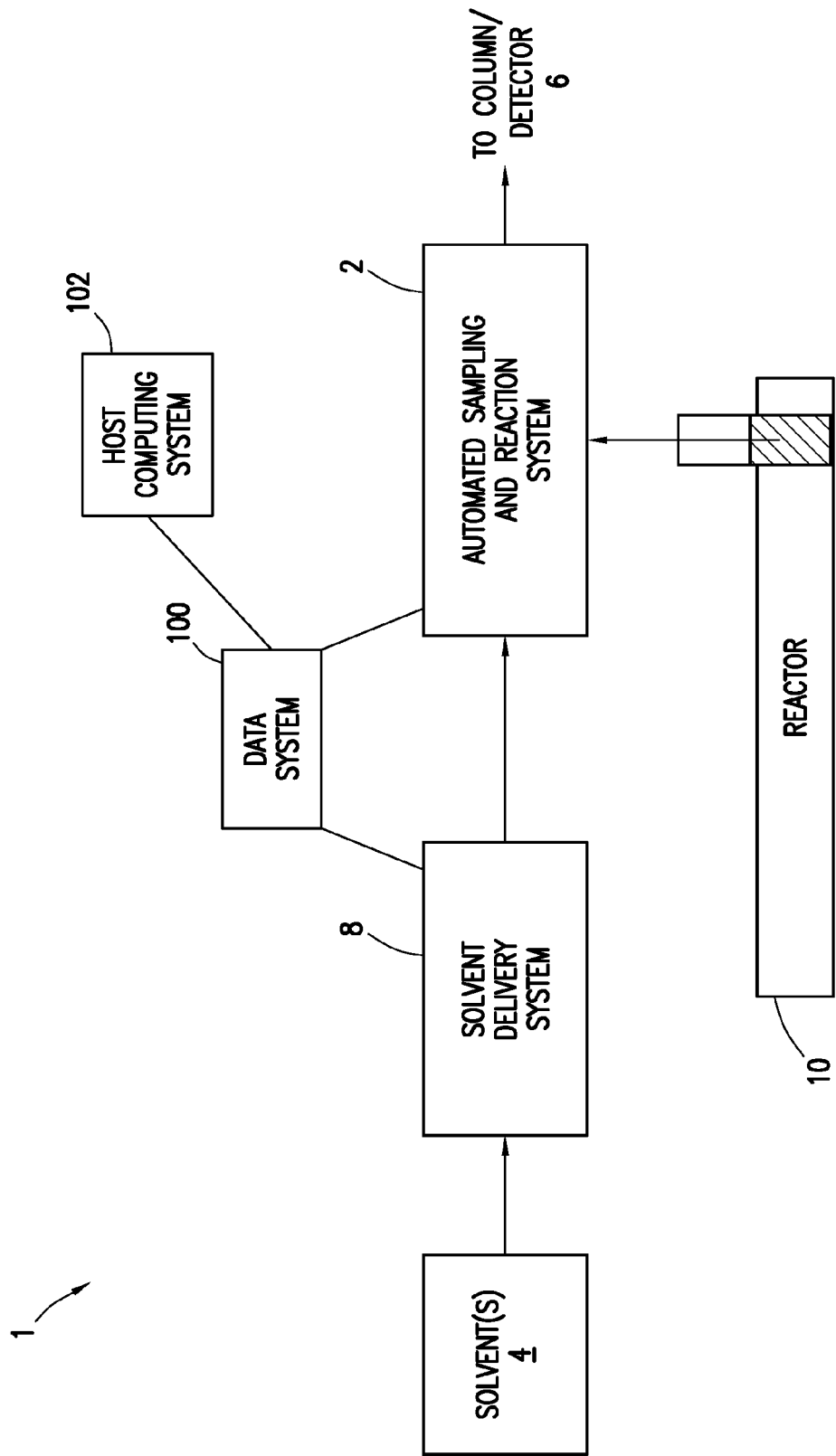
FIG. 1 is a block diagram showing an automated sampling and reaction system utilizing the valve and pump assembly together with microreactor presented herein.

Automated sampling and reaction systems for high pressure liquid chromatography or detectors for a wide variety of applications including, but not limited to, protein and peptide identification and quantitation, monitoring and analysis of cell culture media and nutritional content of food and feed are provided herein. The need to interface synthetic organic reactions from either batch reactors or continuous flow reactors has been identified. The sample being analyzed can be drawn from reactors of different sizes and can require dilution to maintain solubility or decrease the amount of material being introduced into the chromatographic system to maintain a response from the detector. In other instances, the samples being withdrawn from the process may be environmentally unstable and any manual manipulation may result in the degradation of sample prior to analysis. In other instances, the reproducibility of a consistent sample being withdrawn independent of the operator results in a more reproducible result.

Well-established chromatography technologies include High Performance Liquid Chromatography ("HPLC"), Ultra Performance Liquid Chromatography ("UPLC") and Supercritical Fluid Chromatography ("SFC"). HPLC systems use high pressure, ranging traditionally between about 1,000 psi (pounds per square inch) to approximately 6,000 psi, to generate the flow required for liquid chromatography in packed columns. In contrast to HPLC, UPLC systems use columns with smaller particulate matter and higher pressures approaching 20,000 psi to deliver the mobile phase. SFC systems use highly compressible mobile phases, which typically employ carbon dioxide ($CO_2$) as a principle component.

The automated sampling and reaction systems described herein can deliver turn-key analysis that can be optimized for high pressure liquid chromatography process and detection. The disclosed systems can be used with different types of detectors including mass spectrometry ("MS"), tunable ultraviolate/visible ("TUV"), photodiode array ("PDA"), evaporative light scattering, multi-angle light scattering, refractive index, conductivity, charged aerosol, chemiluminescent nitrogen detector ("CLNC"), electrochemical circular dichroism, polarimeter, nuclear magnetic resonance ("NMR"), or fluorescent ("FLR") detectors. The automated sampling and reaction systems are also useful for application-specific performance qualification, providing the same result: day-to-day, instrument-to-instrument, lab-to-lab around the world.

The automated sampling and reaction system comprises an external sampling valve, microreactor, priming valve, reagent valve, injection valve and a pumping system. The automated sampling and reaction system may further comprise a mixing tee and diluent valve. The pumping system has one or more pumps working in combination with the valves to draw and discharge sample, diluent and/or reagent into the microreactor for subsequent injection into a solvent composition stream. The pumping system may include a sample pump, a diluent pump and/or a reagent pump.

More specifically, the external sampling valve is connected to the priming valve, the mixing tee and a collection reservoir. The mixing tee is connected to the microreactor and the diluent valve. The microreactor is connected to the reagent valve and the injection valve. Sample reacts in the microreactor with reagent, diluent or other compounds to form a secondary sample which is then discharged into a solvent composition stream flowing to the injection valve via a second sample loop. The combination of secondary sample and solvent composition stream is then discharged to the liquid chromatography column or detector.

As described herein, the external sampling valve has two configurations. In a first configuration, the external sampling valve is configured to draw a discrete amount of sample or continuous sample from a reactor or reactor flow stream. In a second configuration, the external sampling valve discharges drawn sample via wash discharged from the sample pump to the mixing tee. Similarly, the reagent valve has two configurations. In a first configuration, the reagent valve draws reagent from a reagent reservoir. In a second configuration, the reagent valve discharges reagent into the microreactor for reacting with sample. In addition, the priming valve has two configurations. In a first configuration, wash is drawn into the priming valve and in a second configuration, wash is discharged from the priming valve into the external sampling valve. Likewise, the injection valve has two configurations. In a first configuration, secondary sample is injected into the solvent composition stream, or if secondary sample has not yet been loaded into the second sample loop of the injection valve, a solvent composition stream flows through the second sample loop. In the second configuration of the injection valve, secondary sample flows through the second sample loop and solvent composition stream flows through the valve and out to a column or detector. Finally, when sample requires dilution, the diluent valve is provided and has two configurations. In a first configuration, the diluent valve is configured to draw diluent from a diluent reservoir. In a second configuration, the diluent valve discharges diluent to the mixing tee.

These automated sampling and reaction systems couple the process analysis system with novel flow reactor technology to enable continuous, online analysis of sample where sample preparation prior to analysis is required such as derivation, quenching and/or other types of sample preparation. As described herein, triggering of an analysis draws sample from the reactor or reactor flow stream into the microreactor with or without prior dilution. The same trigger can launch the appropriate reagents to be pumped into microreactor.

As used herein, "online" means that the automated sampling and reaction system is connected directly to a process (or production) line to acquire samples from the process line in approximately real time without manual intervention, then dilute, derivatize, load, and inject the acquired process samples for subsequent chromatographic analysis. The chromatographic analysis thus occurs in parallel to the continued operation of the process line. No distinction is made here between a production line and a process line.

An "at-line" system means that the system is physically near but unconnected to the process line from which an individual acquires a process sample manually, carries and places the process sample into the system for processing.

An "in-line" system is one that is physically incorporated within the process line (i.e., the chromatographic analysis and process line operations in this instance are akin to serial processing), and can also refer to the direct real time detection process such as temperature, pressure or spectroscopy (such as raman and infrared) where the probes used are in direct contact with the process.

Advantageously, the systems and methods described herein increase reproducibility of the sample preparation and analysis, reduce variability due to handling, reduce the number of steps and manual manipulations of the sample by the operator, reduce the overall time and effort required to prepare the sample, improve throughput and decrease the opportunity for imprecision and accuracy errors by the operator. The present systems and methods do not require separate containers in order to prepare a sample for injection to a detector or perform the dilution, quenching or derivatization. Contamination is avoided and smaller amounts of sample are needed for preparation and analysis.

Moreover, the automated sampling and reaction systems described herein provide online, synchronized addition of multiple reagents to samples at optimal timing, concentration, temperature, and flow rate and with minimal interruption to sample preparation (i.e. allowing continuous sample preparation) prior to the injection into the column or detector. These systems and methods provide a controlled environment via the use of a microreactor in order to modify and/or convert sample by one or more reagents. The amount of sample consumed is reduced and sampling is less disturbing to the process.

There are other advantages of the methods and systems disclosed herein. First, while sample volume must be sufficient to be transferred from the reactor to the injection valve, with the present systems and methods, sampling is largely undisturbed. These systems are designed to minimize sample diffusion. Using a back wash, sample travels in the middle of the tubular flow and, therefore, diffusion of sample at the edges of the tubing goes to waste and is not representative of the sample. The volume of sample diffused is minimized and dispersion of the sample avoided. The sample largely remains intact. In addition, the amount of sample required for the detector is minimized because of the low rate of dispersion of sample into the wash.

The Separation and Detection Systems

FIG. 1 is a block diagram of a separation and detection system 1 for separating a mixture into its constituents as provided herein. Useful separation and detection systems 1 include liquid chromatography systems, supercritical fluid chromatography systems, capillary electrophoresis, gas chromatography systems, mass spectrometerslCP-MS/ atomic adsorption source systems, fluorescence detection, UV detection, UV-Visible spectroscopyisible, a cuvette, NMR tube or electromechanical. The separation and detection system 1 as described herein includes an automated sampling and reaction system 2 and a solvent delivery system 8. The automated sampling and reaction system 2 is in fluidic communication with a reactor 10 or a reactor flow stream (not shown). The automated sampling and reaction system 2 is also in fluidic communication with a solvent delivery system 8. The solvent delivery system 8 provides a solvent composition stream to the automated sampling and reaction system 2. Subsequently, the solvent composition stream is combined with sample and sent to, and received by, a chromatographic column 6 or detector (not shown). The separation and detection system 1 by way of the automated sampling and reaction system 2 is directly connected to the reactor 10 or other vessel or reactor flow stream or other process line by tubing. The automated sampling and reaction system 2 can automatically or manually acquire samples from the reactor 10 or the reactor flow stream (not shown).

The automated sampling and reaction system 2 can acquire sample from a point on a process flow stream, a reactor flow stream or directly from the reactor. The automated sampling and reaction system 2 can acquire samples continuously or at different stages (location and/or time-based) of the manufacturing process. For example, the sample can be acquired at different time intervals in order to derivatize sample during varying stages of the process. In general, the reactor 10 or other vessel and/or the reactor flow stream or other process lines are representative of various process sources including manufacturing processes, beaker reactions, exit lines (cleaning validation), reaction chamber and fermentation reactions.

Importantly, the automated sampling and reaction system 2 allows for sample preparation to form a suitable secondary sample for measurement by the detector. Typically, sample preparation is an essential part of chromatographic and spectroscopic analyses. The methods and systems provided herein provide a representative, reproducible and homogenous solutions that are suitable for injection into the column for chromatographic analysis, or into an ICP-MS/ atomic adsorption source or into a cuvette or NMR tube for further characterization.

Using the systems and methods described herein, sample preparation provides an aliquot that is relatively free of interferences and will not damage the column or instrument and is also compatible with the analytical method. In chromatography applications, sample can be injected onto a chromatography column without affecting sample retention or resolution or the stationary phase itself, and without interfering with detection. Hence, it desirable to concentrate the analytes and/or derivatize them for improved detection or better separation. In spectroscopy, samples should be free of particulates, compatible with spectroscopic sources and have appropriate viscosity to flow into a nebulizer. In short, there are many types of sample preparation protocols used in chromatography and spectroscopy and diverse methods used. However, the systems and methods provided herein are able to accommodate most protocols and methods for sample preparation.

Furthermore, the automated sampling and reaction system 2 described herein can be located a substantial distance from the column 6 or detector (not shown). As such, the term "remote" as used herein simply means separate (i.e. a separate module) or detached. The term remote is not intended to mean that the automated sampling and reaction system 2 is isolated from or otherwise positioned or located a significant distance away from the column 6 or the detector (not shown), and/or the reactor 10 or reactor flow stream. Hence, the devices and methods described herein may include those situations where the automated sampling and reaction system 2 is close to or in proximity to the column 6 or the detector, and to the reactor 10 or reactor flow stream.

The solvent delivery system 8 can include a low-pressure pumping system (not shown) in fluidic communication with reservoirs 4 from which the pumping system draws liquid solvents through tubing (not shown). In a low-pressure pumping system, the mixing of solvents typically occurs before the pump (not shown). The solvent delivery system 8 also may have a mixer (not shown) in fluidic communication with the solvent reservoirs 4 to receive various solvents in metered proportions. This mixing of solvents occurs in accordance with an intake profile, and produces a solvent (mobile phase) composition that remains unchanged (isocratic) or varies over time (gradient). Hence, the pumping system of a solvent delivery system 8 is in fluidic communication with a mixer and can draw a continuous flow of solvent mixture therefrom for delivery to the liquid chromatography column 6 or detector (not shown). To draw and deliver the solvent mixture, the pumping system can, for example, provide a flow rate in the range of about 0.010 ml/min to about 2 ml/min at about 15,000 psi. On the other hand, the flow rate can be a "nano flow" (or down to 200 nL/min) or an HPLC flow (analytical 10 mL/min and preparative to 20-50 mL/min) having pressures from 1000 psi to 20,000 psi. Examples of pumping systems that can be used to implement the pumping system include, but are not limited to, the ACQUITY HPLC Binary Solvent Manager, manufactured by Waters Corp. of Milford, Mass. See, e.g., US 2012/0303167 at ¶ [0019]. Other useful examples of pumping systems include, but are not limited to, single piston pump solvent delivery systems, dual piston reciprocating pump systems, alternative binary pumps, quaternary pump solvent delivery systems, and ternary pump systems.

Hence, by way of example, the solvent delivery system 8 can be a binary solvent manager ("BSM"), which uses two individual serial flow pumps to draw solvents from reservoirs 4 and deliver the solvent composition stream to the automated sampling and delivery system 2. Here, each of the BSM's two independent pumps contains two linear-drive actuators. Each actuator pair comprises a single reciprocating serial pump that delivers precise flow of a single solvent. The two pump systems combine their two solvents 18 at a filter/tee mixer. From there, the solvent mixture flows into the automated sampling and reaction system 2. A gradient elution program is commonly used so that the eluent composition (and strength) is steadily changed during the analysis. This increases separation efficiency, decreases the retention time and improves peak shape by minimizing tailing. See, e.g., T Jiang Y, Viadya L, *The Waters ACQUITY® Ultra-Performance Liquid Chromatograph and the Micromass Quatro Premier Triple Quadrupole Mass Spectrometer*, December, 2012.

The separation and detection system 1 may also include a data system 100 that is in signal communication with the automated sampling and reaction system 2 and the solvent delivery system 8. The data system 100 has a processor and a switch (not shown), e.g., an Ethernet switch for handling signal communication between the solvent delivery system 8 and the automated sampling and reaction system 2. In addition, the data system 100 is programmed to implement the various phases of operation performed by the automated sampling and reaction system 2 (e.g. turning pumps on and off, rotating valves) in order to automatically acquire, dilute, quench and/or derivatize a process sample and introduce the treated process sample to the solvent composition stream, as described herein. Furthermore, a host computing system 102 is in communication with the data system 100, by which the user can download various parameters and profiles to affect the data system's performance.

The Automated Sampling and Reaction System

The automated sampling and reaction system described herein can sample from concentrated reactions and dilute sample over a wide range. For example, sample dilution can range from about 1 to 99 units of diluent to 1 unit of sample. However, dilution range of sample can extend to about 5000 to 1, depending on the accuracy of the remote pump. The automated sampling and reaction system also allow sample quenching, if needed. In these systems, sample is prevented from contacting pumps which increases pump life due to the lack of harsh conditions and prevents contamination. The automated sampling and reaction system 2 can process sample volumes of about 100 μl.

As shown in the figures, the separation and detection system 1 includes automated sampling and reaction system 2, a solvent delivery system 8 and a column 6 or a detector. The automated sampling and reaction system further includes an external sampling valve 22, a priming valve 24, a diluent valve 26, a reagent valve 28 and an injection valve 30. In addition, the automated sampling and reaction system 2 further includes a sample pump 32, a diluent pump 34 and a reagent pump 36, a mixing tee 18 and a microreactor 12.

Each of the valves is a separate, independently operable rotary valve having a plurality of fluidic ports and one or more flow-through conduits. Although described primary as rotary valves, any one or more of these valves: priming, sampling, process-selection, and/or injection, can be other types of valve including, but not limited to, slider valves, solenoids, and pin valves. Each flow-through conduit provides a pathway between a pair of neighboring fluidic ports. When a given valve rotates, its flow-through conduits move clockwise or counterclockwise, depending upon the valve's direction of rotation. This movement operates to switch the flow-through conduit to a different of neighboring fluidic ports, establishing a fluidic pathway between that different pair while removing the pathway from the previously connected pair of fluidic ports.

Further, the valves are sometimes described herein with respect to a particular configuration and rotation thereof, especially as it may relate to the processing of sample within the automated sampling and reaction system 2. However, the valves, including the external sampling valve 22, the priming valve 24, the diluent valve 26, the reagent valve 28 and the injection valve 30, could each rotate in an opposite direction from that which is described herein and shown in the figures (i.e. clockwise as opposed to counterclockwise or counterclockwise as opposed to clockwise) and still accommodate the same functionality and overall workings of the automated sampling and dilution system 2 provided herein. In short, the valves and the operation of the valves are not limited to the manner of rotation or a specific configuration described herein.

In addition, unless otherwise specified, all connections are fluidic and provide for fluid flow, including but not limited to, tubing connections between fluidic ports and devices such as the reactor, the reactor flow stream, valves, pumps, reservoirs and other apparatus that are described herein. Such connections are typically made via tubing ranging in size from 0.005 to 0.150 inches and made of stainless steel, PEEK, Teflon, and/or any material suitable for the pressure and composition of the sample. Also, flow-through conduits are fluidical connections where the ports and conduits are fluidically connected to each other and/or other devices described. Hence, when it is stated that a device, fluidic port or flow-through conduit is connected or in fluidic communication with the other, this means and should be understood to mean that such connection is fluidic unless otherwise noted.

The external sampling valve 22 has a first sample loop 40, six fluidic ports 22-1, 22-2, 22-3, 22-4, 22-5 and 22-6 and three flow-through conduits 22-11, 22-12 and 22-13. The first sample loop 40 connects fluidic ports 22-1 and 22-4. Tubing connects fluidic port 22-2 to the reactor 10. Tubing connects fluidic port 22-3 to a collection reservoir 44. Tubing connects fluidic port 22-5 to fluidic port 24-1 of the priming valve 24. Further, tubing connects fluidic port 22-6 to the mixing tee 18. As shown in FIG. 2, in the idle configuration, sample pump 32, diluent pump 34 and reagent pump 36 are off and not running. However, sample could flow into fluidic port 22-1 into the external sampling valve 22 through flow-through conduit 22-11 and out fluidic port 22-1 into the first sample loop 40 even when not sampling. If reactor or process flow stream operates under pressure, sample may flow out of the first sample loop 40 into fluidic port 22-4 through flow through conduit 22-12 out fluidic port 22-3 and into the collection reservoir 44.

Similarly, the injection valve 30 has a second sample loop 42, six fluidic ports 30-1, 30-2, 30-3, 30-4, 30-5 and 30-6 and three flow-through conduits 30-11, 30-12 and 30-13. The second sample loop 42 connects fluidic ports 30-1 and 30-4. Tubing connects fluidic port 30-2 to a waste reservoir 38. Tubing also connects fluidic port 30-3 to the microreactor 12. Further, tubing connects the solvent delivery system 8 to fluidic port 30-5. Also, tubing connects fluidic port 30-6 to the column 6 or a detector (not shown). Flow-through conduit 30-11 provides a fluidic pathway between fluidic port 30-1 and fluidic port 30-6. Similarly, flow-through conduit 30-13 provides a fluidic pathway between fluidic port 30-4 and fluidic port 30-5. The injection valve 30 has the capacity to handle volumes of 10 micoliters to 100 microliters and can be scaled.

During operation, the solvent delivery system 8 should be on in order to maintain minimal disturbance to the solvent composition stream and to provide a solvent composition stream having a fluidic pathway into fluidic port 30-5 through flow-through conduit 30-13 out fluidic port 30-4 through the second sample loop 42. This solvent composition stream fluidic pathway can continue into fluidic port 30-1 through flow-through conduit 30-11 and out fluidic port 30-6 to the column 6 or detector (not shown).

As shown in the figures, the priming valve 24 has seven fluidic ports 24-1, 24-2, 24-3, 24-4, 24-5, 24-6 and 24-7 and one flow-through conduit 24-11. Tubing connects fluidic port 24-6 to a wash reservoir 46. Tubing also connects fluidic port 24-7 to the sample pump 32. Tubing further connects fluidic port 24-1 to fluidic port 22-5 of the external sampling valve 22.

Similarly, the diluent valve 26 has seven fluidic ports 26-1, 26-2, 26-3, 26-4, 26-5, 26-6 and 26-7 and one flow-through conduit 26-11. Tubing connects fluidic port 26-6 to a diluent reservoir 48 and fluidic port 26-7 to the diluent pump 34. Tubing further connects fluidic port 26-1 to the mixing tee 18.

The reagent valve 28 also has seven fluidic ports 28-1, 28-2, 28-3, 28-4, 28-5, 28-6 and 28-7 and one flow-through conduit 28-11. Tubing connects fluidic port 28-6 to a reagent reservoir 50 and fluidic port 28-7 to the reagent pump 36. Tubing also connects fluidic port 28-1 to the microreactor 12.

The sample pump 32, the diluent pump 34 and the reagent pump 36 are each positive displacement pumps. During startup, a liquid positive displacement pump cannot simply draw air until the feed line and pump fill with the liquid that requires pumping. Typically, an operator must introduce liquid into the system to initiate the pumping. While loss of prime is usually due to ingestion of air into the pump, the clearances and displacement ratios in pumps for liquids and other more viscous fluids usually cannot displace air due to its lower compressibility. In the present assembly, however, the priming valve 24, the diluent valve 26 and the reagent valve 28 replace the need for manually introducing liquid into the sample pump 32, the diluent pump 34 and the reagent pump 36.

The automated sampling and reaction system 2 can be used to monitor any process or reaction where the reactor or the reactor flow stream is near or far away. The size and length of the tubing required can be mathematically represented as follows:

$$\Delta p = 8 * \rho * (V^2)/(\pi^2 * D^4) * \kappa * L/D * 0.00014504, \text{ where}$$

$\rho$=solvent density (kg/m$^3$)
V=flow velocity (m$^3$/s)
D=tube diameter (m)
$\lambda$=Coefficient of friction
L=length of tube
0.00014504=kPa to psi Sample can be drawn from a reactor 10 or reactor stream operating under pressure or for a non-pressurized reaction where the reactor or other vessel is not operating under pressure (greater than about 1 atmosphere or 14.7 psi at sea level). The automated sampling and reaction system 2 described herein dilutes sample at the mixing tee 18. However, this system 2 can work without sample dilution. Likewise, reagent can be reacted with diluted or un-diluted sample in the microreactor 12 prior to injection of the sample into the column 6 or detector. However, the automated sampling and reaction system 2 can simply provide a direct sample load to the injection valve 30 without sample dilution or addition of reagent.

Sample volume must be large enough to be transferred from the reactor 10 to the injection valve 30. In the present system 2, sample flow is largely undisturbed and unaffected by the system 2. However, if the sample is first diluted, a larger volume is created and sample can be transferred farther before unacceptable levels of diffusion are reached. For example, although the ends of a sample band undergo diffusion, the middle portion of the sample band away from the ends will remain unaffected. A diluted sample will have a larger volume of sample away from the ends that is unaffected by diffusion in comparison to an undiluted sample. A diluted sample can therefore be moved farther than an undiluted sample. Furthermore, because tubing diameters are narrow, sample diffusion is minimized regardless of distance transferred. In the present systems, samples largely remain intact because contact area between sample and solvent is minimized. For example, the diameter of the tubing can be small, e.g., as small as approximately 4 mil (about 100 μm.) Diffusion is a concentration-driven mass transfer process that can be defined as the mass transferred per unit area per unit time. Small diameter tubing provides a corresponding small area over which diffusion can occur, thereby reducing diffusion. With the use of a backwash in the system 2, dispersion of the sample is avoided. In addition, the amount of sample required for the column 6 or the detector (not shown) is minimized because of the low rate of dispersion of sample into the wash.

As shown in figures and described in more detail below, in operation, the solvent delivery system is turned on. Likewise, the sample pump 32, the diluent pump 34 and the reagent pump 36 are turned on and charged (FIG. 2). The sample pump 32 draws wash from the wash reservoir 46 through the priming valve 24 through fluidic port 24-6 into flow-through conduit 24-11 and out fluidic port 24-7. Sample is then drawn from the reactor 10, or other sample source, by the sample pump 32 into the external sampling valve 22 at fluidic port 22-2 creating a fluidic pathway of sample through flow-through conduit 22-11 and out fluidic port 22-1 into the first sample loop 40, and into fluidic port 22-4 through flow-through conduit 22-12 and out fluidic port 22-12 into the collection reservoir 44 (FIG. 3).

Figure 3:
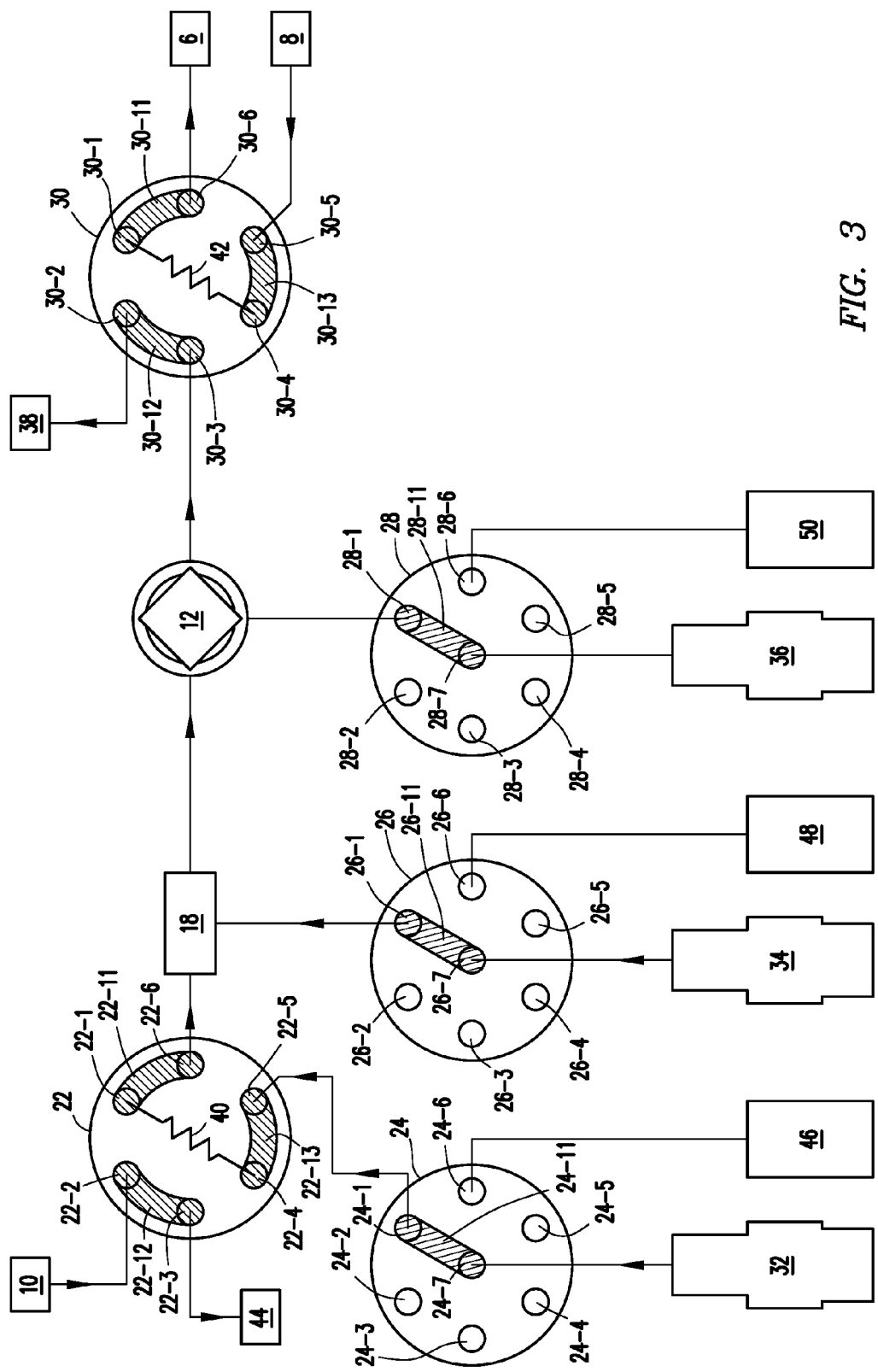
FIG. 3 shows the automated sampling and reaction system configured to dilute sample.

As shown in FIG. 3, to mix sample and dilute, the priming valve 24 and the external sampling valve 22 are rotated so that sample pump 32 discharges wash from the priming valve 24 to the external sampling valve 22 in order to backwash sample transferring to the mixing tee 18. At the mixing tee 18, sample can be mixed with diluent or can simply flow through the mixing tee to the microreactor.

Figure 4:
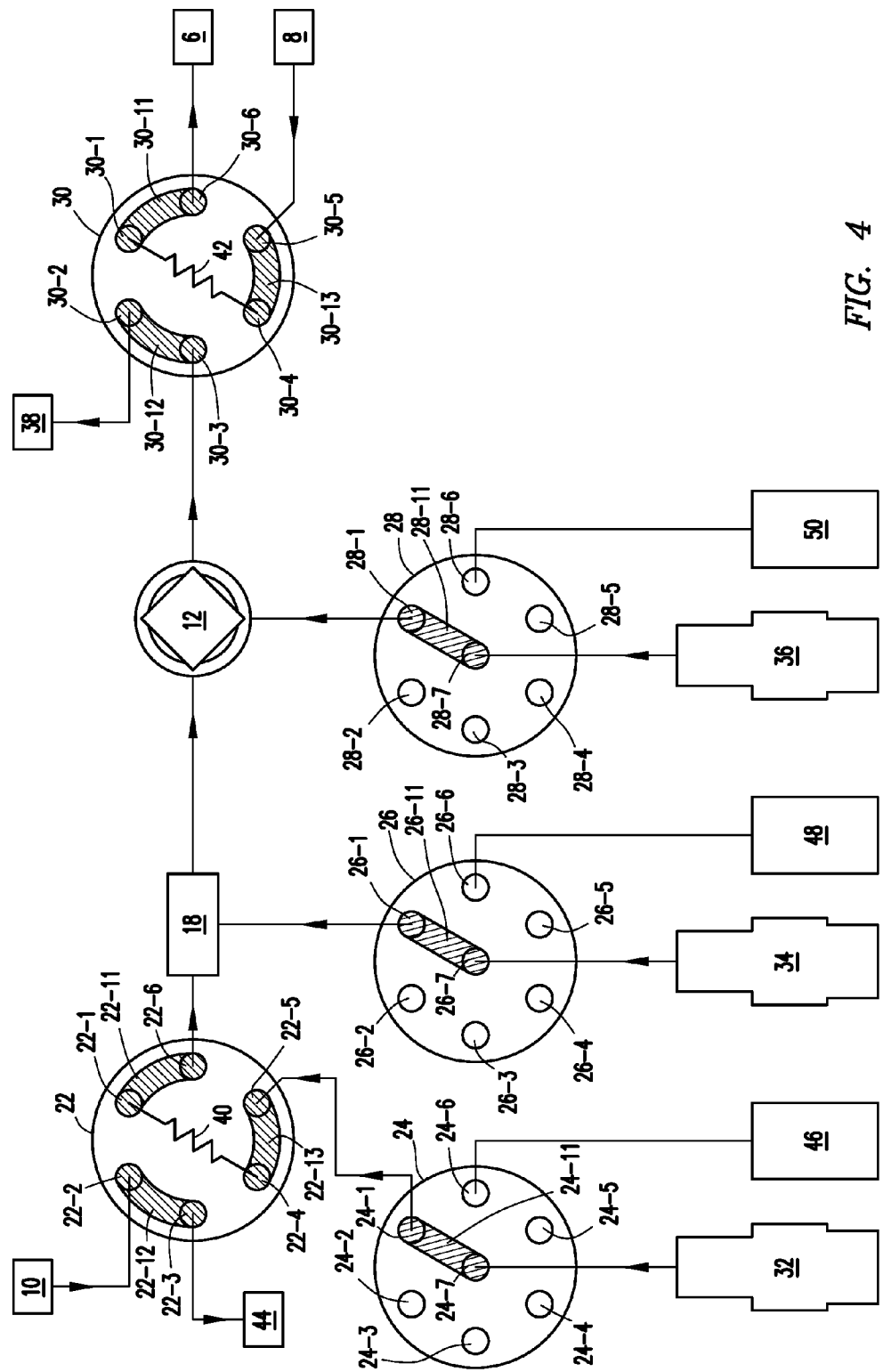
FIG. 4 shows the automated sampling and reaction system configured to derivatize sample.
Figure 5:
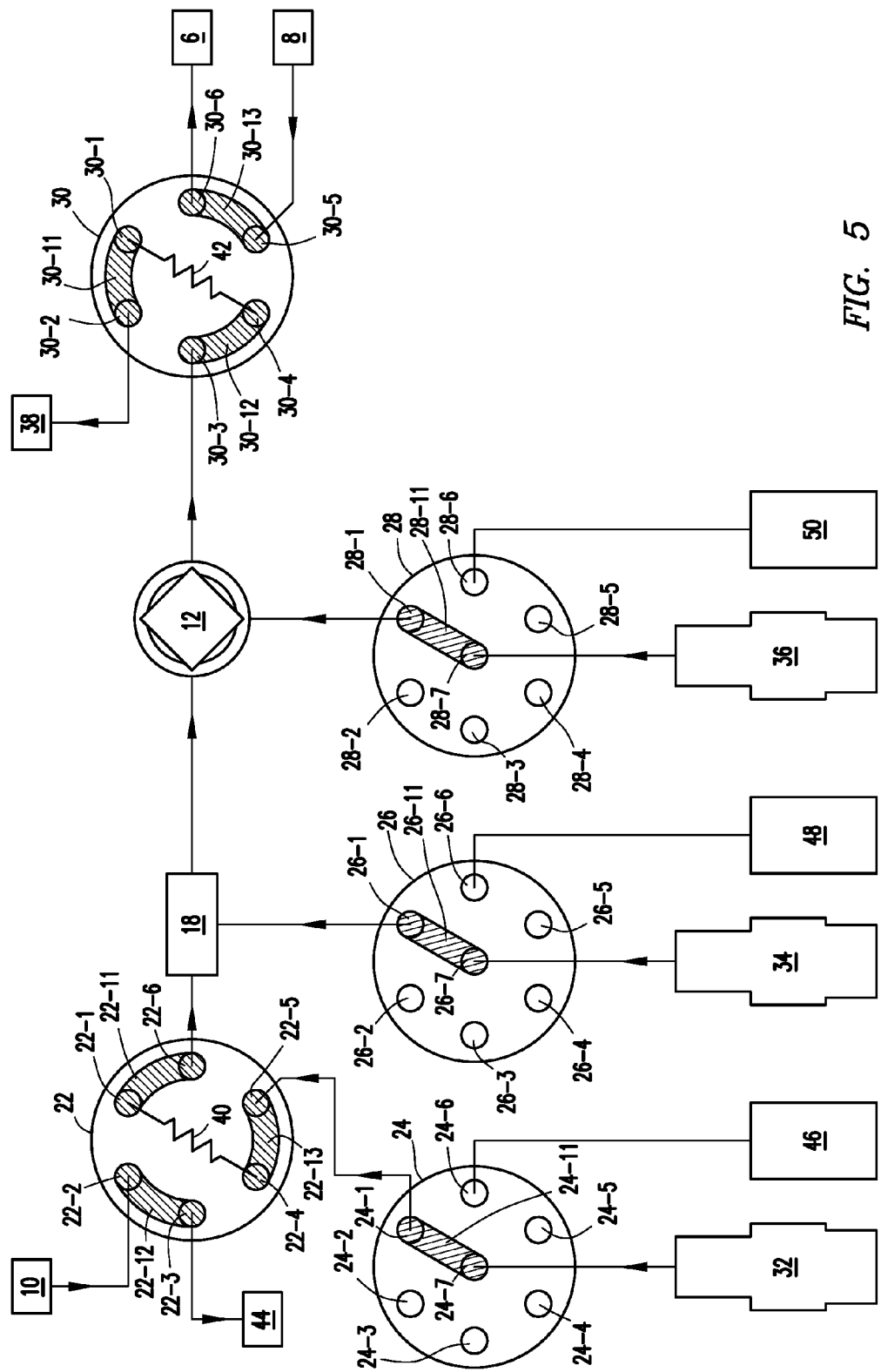
FIG. 5 shows the automated sampling and reaction system configured to load sample into sample loop of the injection valve.
Figure 6:
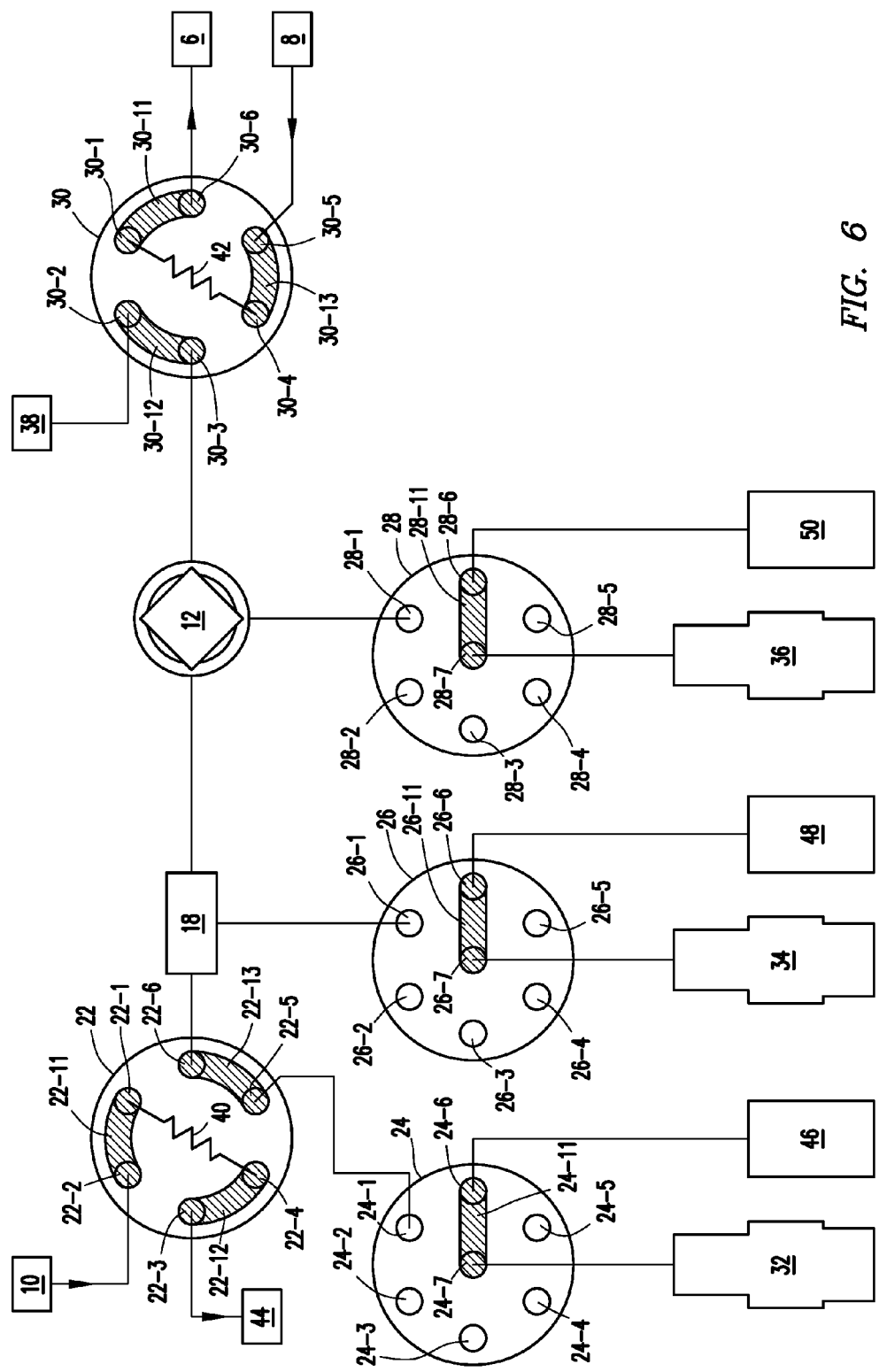
FIG. 6 shows the automated sampling and reaction system configured to inject sample into the solvent composition stream.
Figure 7:
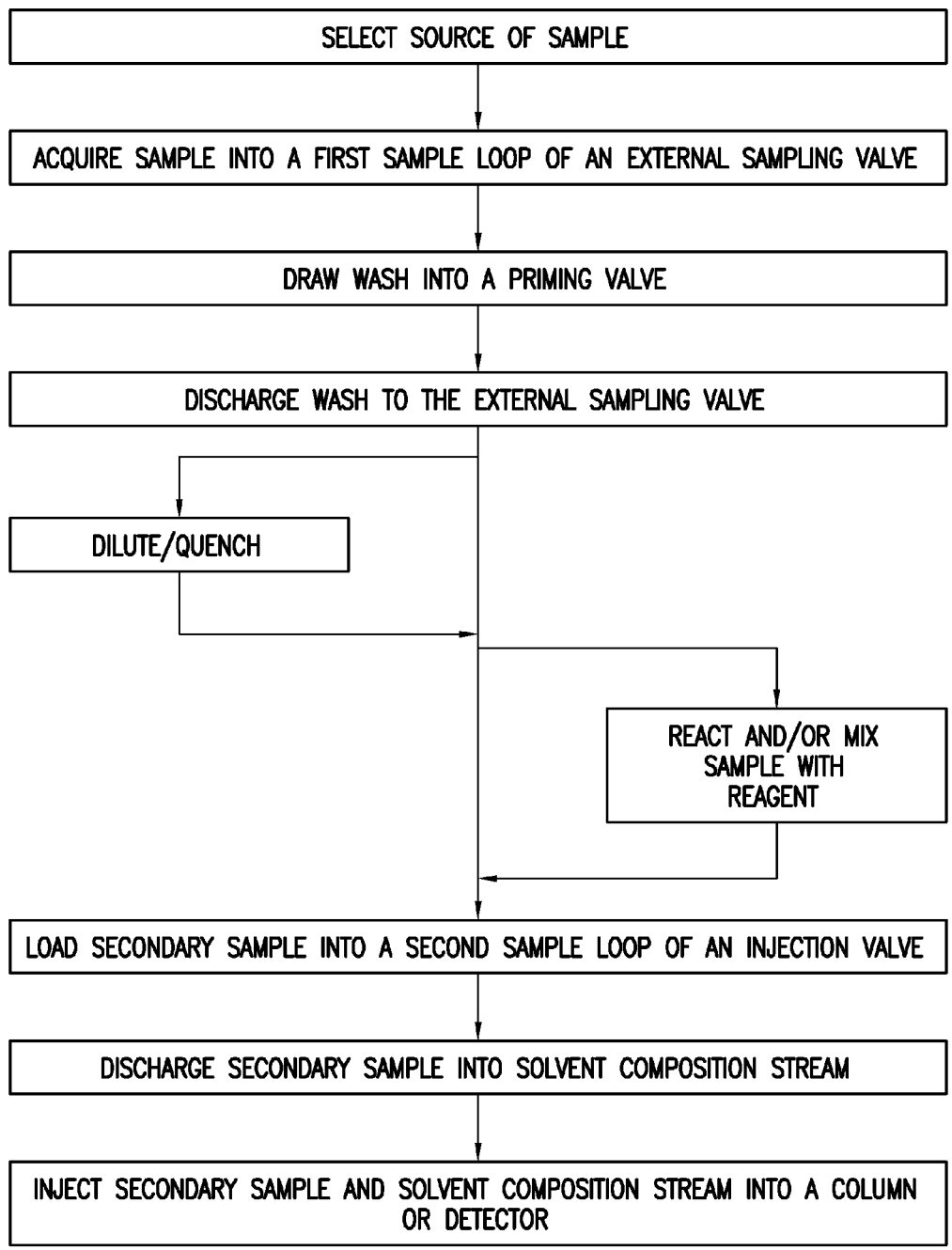
FIG. 7 provides a flow chart depicting the overall flow of the automated sampling and reaction systems and methods of using the same that are described herein.

As shown in FIG. 4, additional sample preparation can occur in the microreactor 12 where sample reacts with a reagent or other reactant which is discharged by the reagent pump 36 through the reagent valve 28. Sample is then sent to the injection valve 30, loaded into the second sample loop 42 and injected into the solvent composition stream pumped from the solvent delivery system 8 (FIG. 5). The sample in the solvent composition stream is pushed to the column 6 or a detector (FIG. 6). During this step, the pumps 32, 34 and 36 can be charged to be ready for next injection.

Sample Collection

As noted above, the priming valve 24 is connected to the sample pump 32 at fluidic port 24-7. The priming valve 24 is also connected to the wash reservoir 46 at fluidic port 24-6. The diluent valve 26 is connected to the diluent pump 34 at fluidic port 26-7 and to the diluent reservoir 48 at fluidic port 28-6. The reagent valve 28 is connected to the reagent reservoir 50 at fluidic port 28-6 and to the reagent valve 36 at fluidic port 28-7.

Figure 2A:
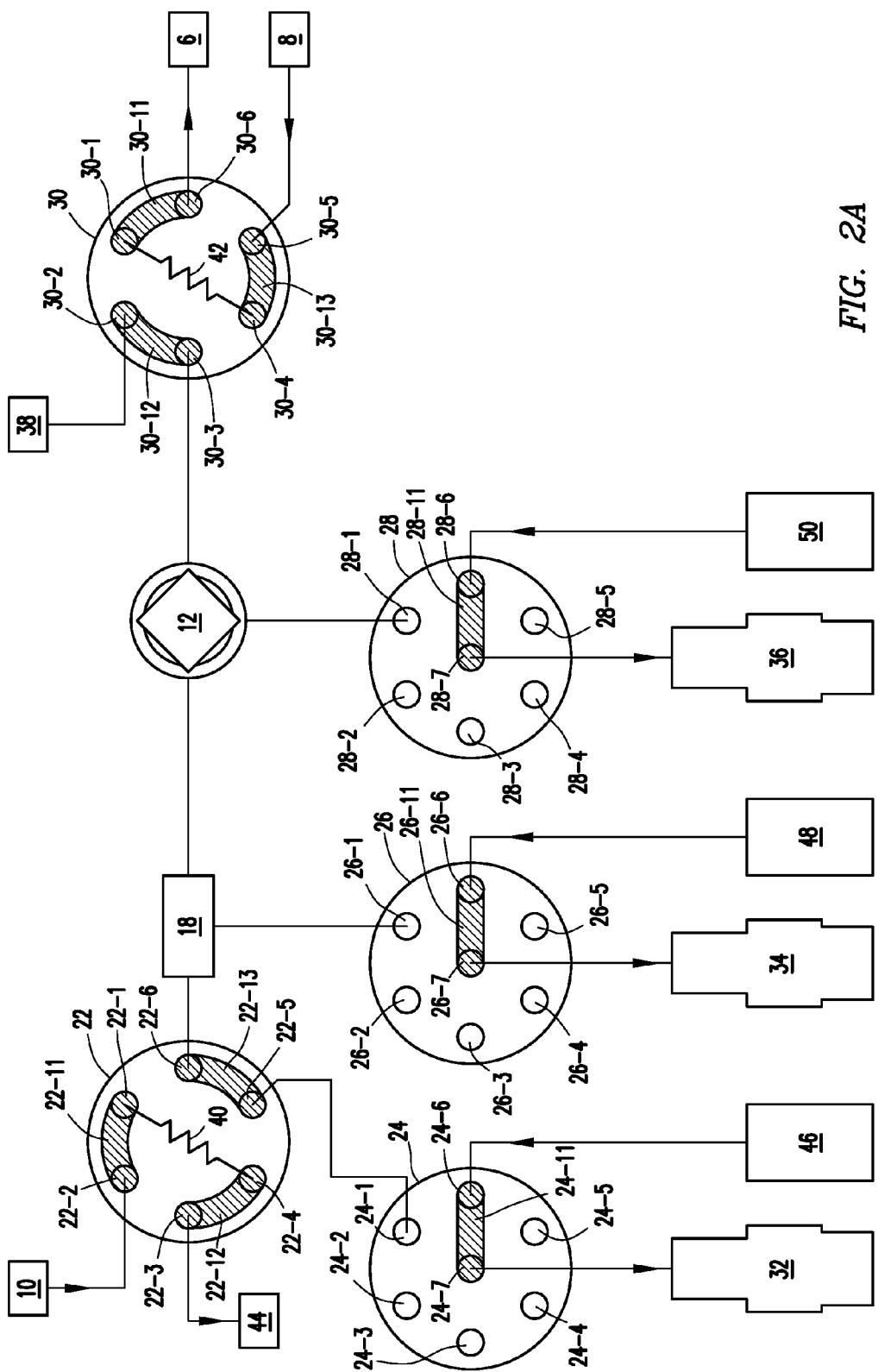
FIG. 2A depicts the automated sampling and reaction system configured to draw sample from a pressurized sample source, to prime the sample pump and to draw diluent and reagent into the diluent pump and reagent pump.

FIG. 2A depicts the automated sampling and reaction system 2 configured to draw sample from the reactor 10 and to draw wash from the wash reservoir 46 into the priming valve 24. For sample collection, the sample pump 32 is turned on and charged. If sample is to be diluted, the diluent pump 34 is also preferably turned on and charged. The reagent pump 36 can also be turned on and charged or can remain off. The sample pump 32, the wash pump 34 and the reagent pump 38 can be turned on and charged in parallel or sequentially.

In addition, during sample collection, the solvent delivery system discharges a solvent composition stream into the injection valve 30 at fluidic port 30-5, where a fluidic pathway is provided from fluidic port 30-5 through flow-through conduit 30-13 into fluidic port 30-4 and through the sample loop 42 into fluidic port 30-1 through flow-through conduit 30-11 and out fluidic port 30-6 to the column 6 or other detector.

For sample collection, as shown in FIG. 2A, the priming valve 24 is configured to provide a fluidic pathway between the sample pump 32 and wash reservoir so that wash is drawn from the wash reservoir 46 into the priming valve 24 at fluidic port 24-6 through the flow-through conduit 24-11 and out fluidic port 24-7 to the sample pump 32. Likewise, in its first configuration the external sampling valve 22 is configured to provide a fluidic pathway between the reactor 10 or other source of sample to the collection reservoir 44 so that sample is drawn or discharged from the reactor 10 through fluidic port 22-2 through flow-through conduit 22-11 and out fluidic port 22-1 through the first sample loop 40 into fluidic port 22-4 through flow-through conduit 22-12 and out fluidic port 22-3 to the collection reservoir 44. Recycling systems and devices can be connected to the collection reservoir 44 or directly to the external sampling valve 22 to allow for the sample to flow back to the reactor, with or without further treatment or processing of the sample.

As also shown in FIG. 2A, the reagent valve 28 can be configured to provide a fluidic pathway between the reagent reservoir 50 and the reagent pump 36 such that the reagent pump 36 draws reagent from reagent reservoir 50. Optionally, the diluent valve 26 can be configured to provide a fluidic pathway between the diluent pump 34 and the diluent reservoir 48. Specifically, a fluidic pathway is provided from the diluent reservoir 48 through the diluent valve 26 at fluidic port 26-6 through flow-through conduit 26-11 and out fluidic port 26-7. As an option, at the sample collection step, the reagent pump 36 draws reagent from the reagent reservoir 50 to the reagent pump 28 through the reagent valve 28 as the flow-through conduit 28-11 provides fluidic pathway between fluidic port 28-6 and fluidic port 28-7. As an option, reagent can be contained in, and drawn from, the diluent reservoir 48 by the diluent pump 34 and therefore, a fluidic pathway of reagent is provided from the diluent reservoir 48 through the diluent valve 26 at fluidic port 26-6 through flow-through conduit 26-11 and out fluidic port 26-7.

Automated Sampling and Reaction System Sampling from a Non-Pressurized Source

Figure 2B:
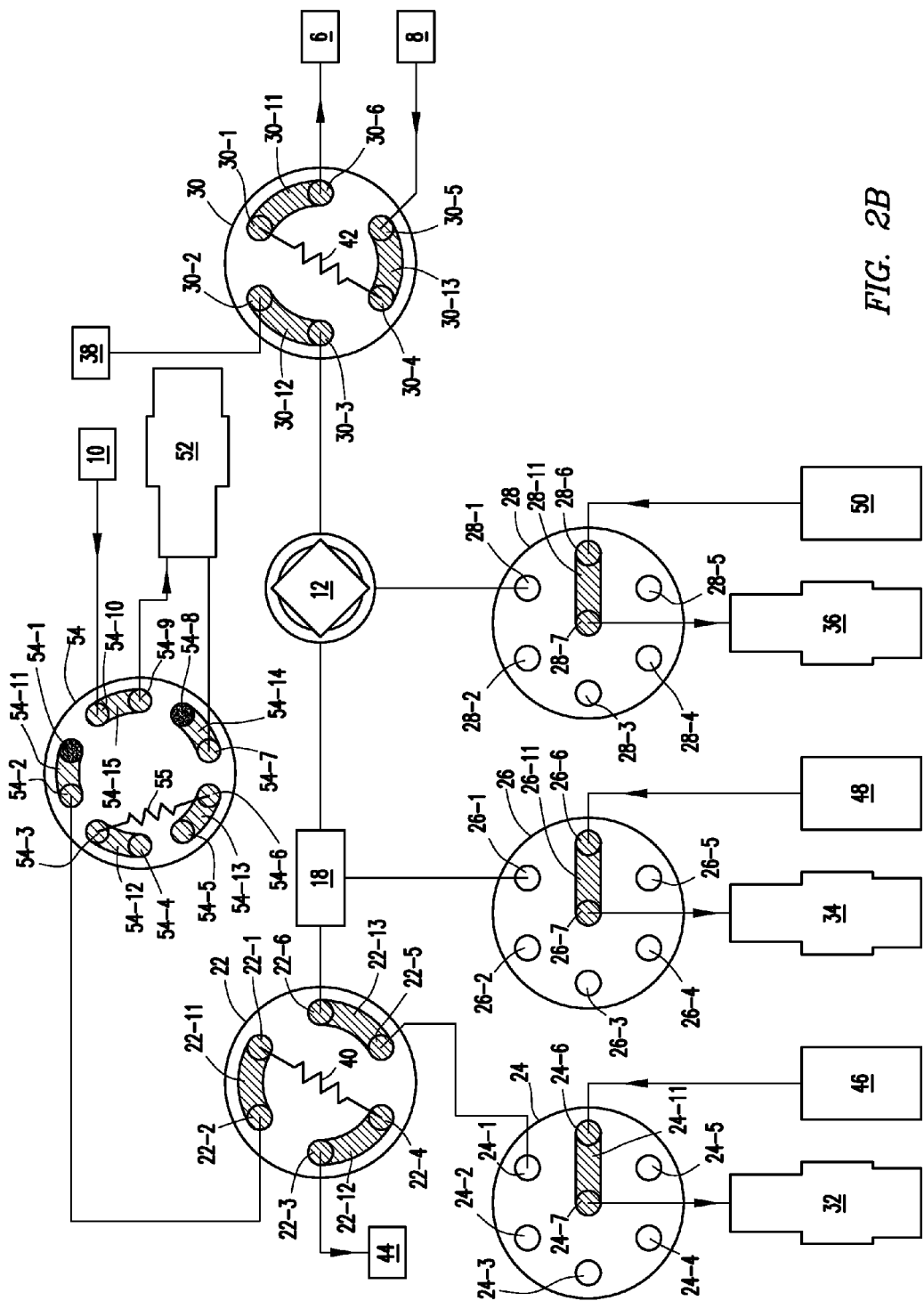
FIG. 2B depicts the automated sampling and reaction system configured to collect sample from a non-pressurized sample source where the external auxiliary valve is in the first configuration.
Figure 2C:
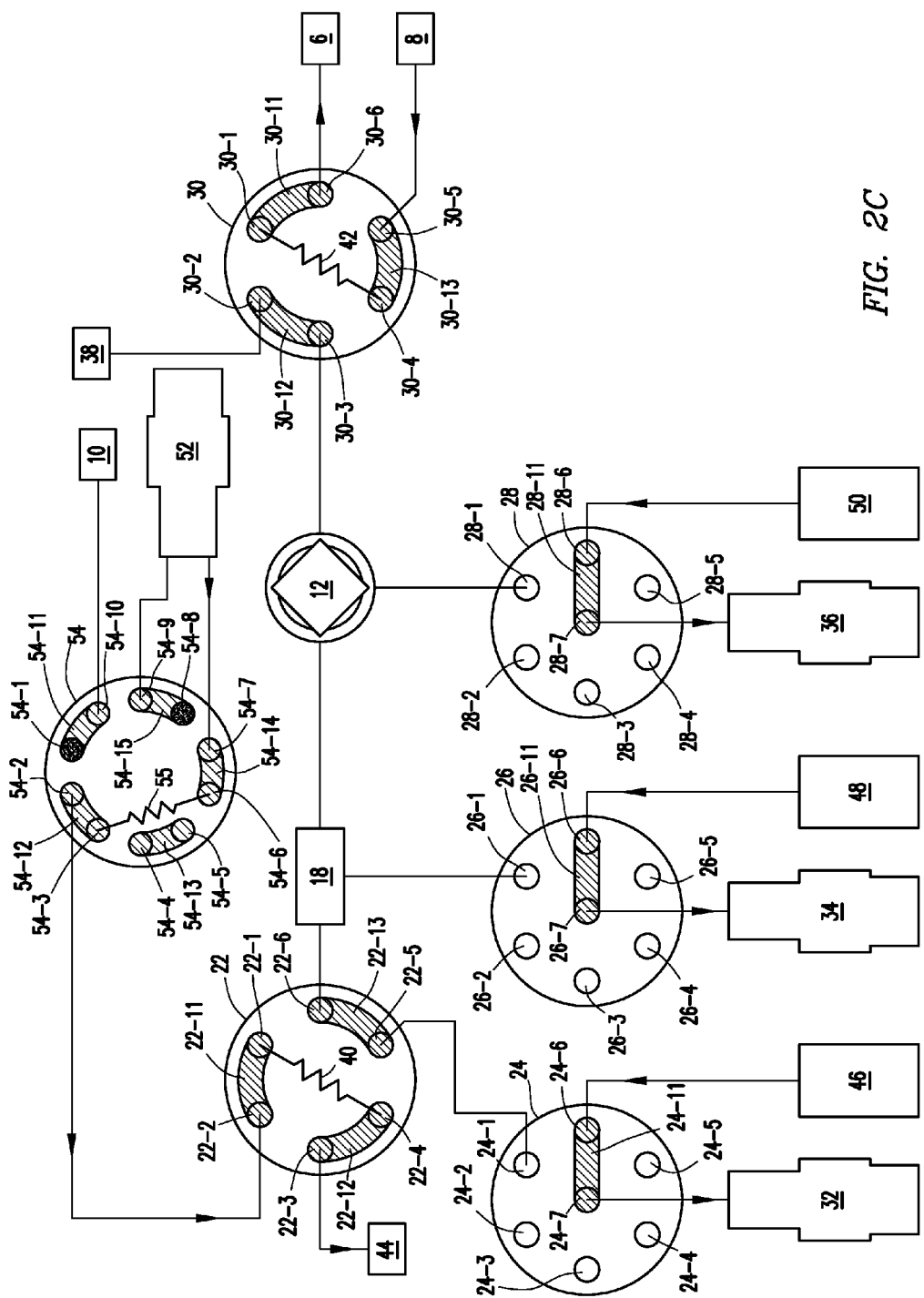
FIG. 2C depicts the automated sampling and reaction system configured to collect sample from a non-pressurized sample source where the external auxiliary valve is in the second configuration.
Figure 2D:
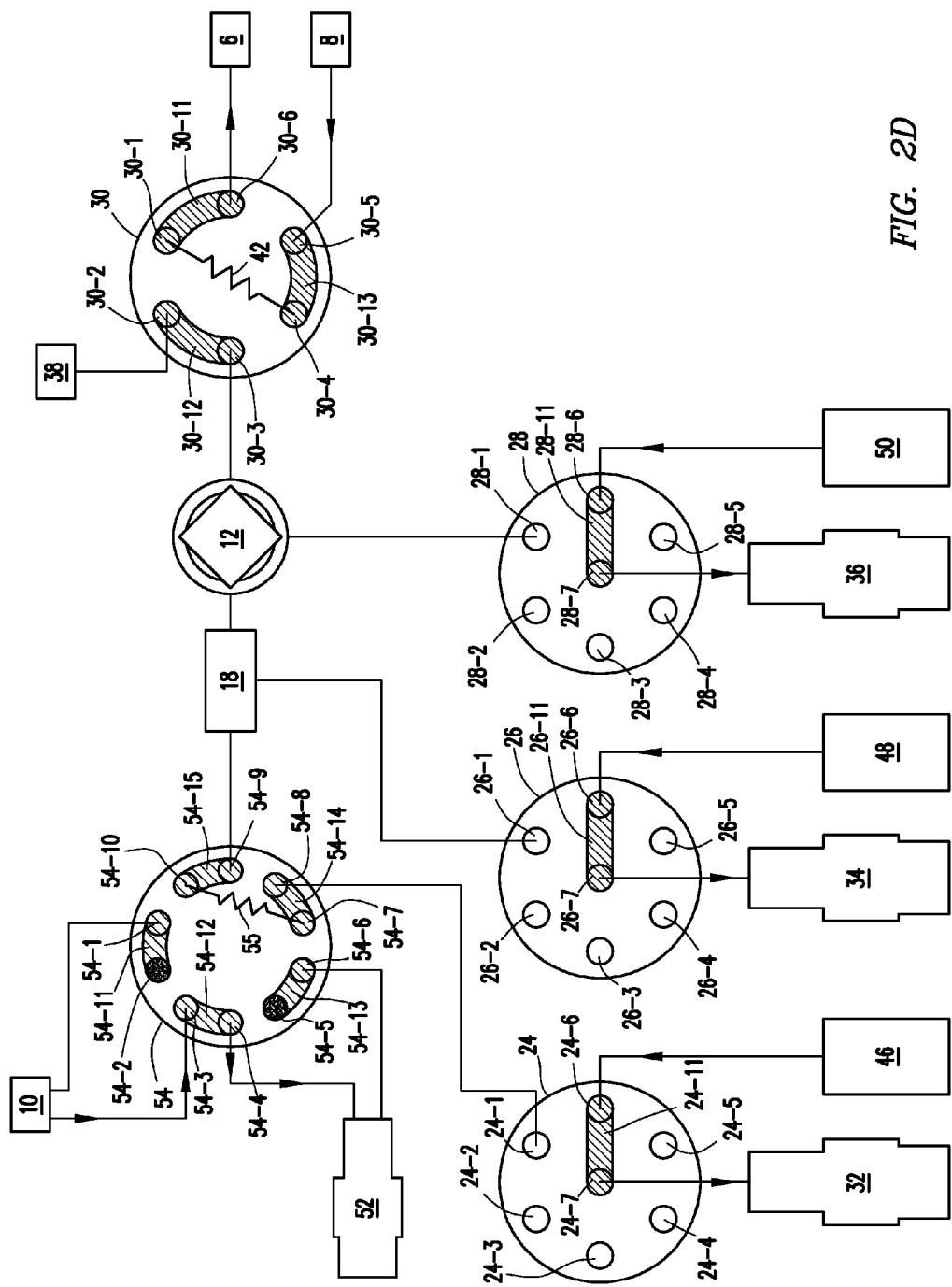
FIG. 2D shows the automated sampling and reaction system configured to collect sample from a non-pressurized sample source where the external sampling valve 22 is replaced with the external auxiliary sampling valve 54 to draw sample and discharge sample from the third sample loop to the mixing tee.
Figure 2E:
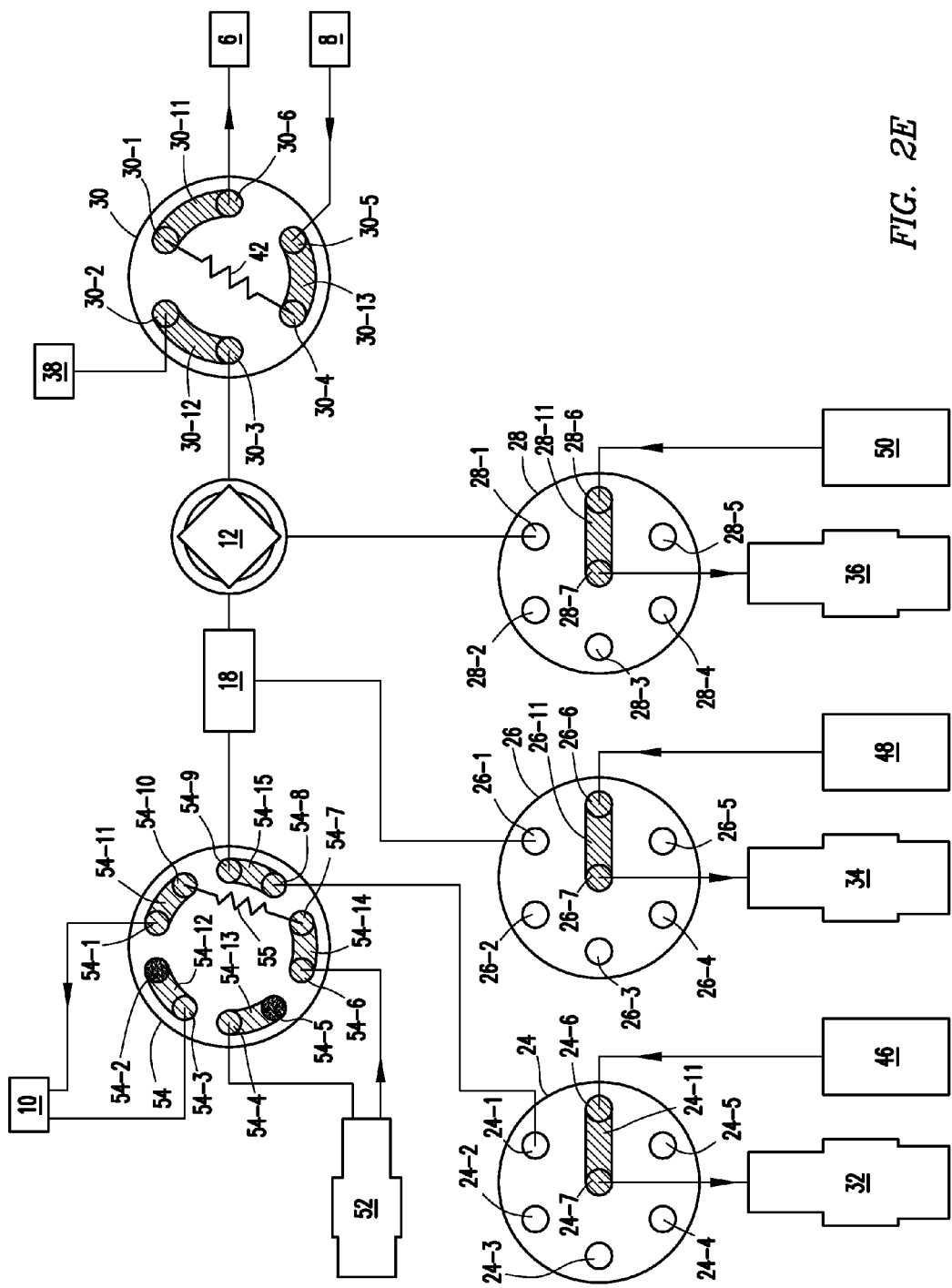
FIG. 2E shows the automated sampling and reaction system configured to collect sample from a non-pressurized sample source where the external sampling valve 22 is replaced with the external auxiliary sampling valve 54 to load sample into the third sample loop.
Figure 2F:
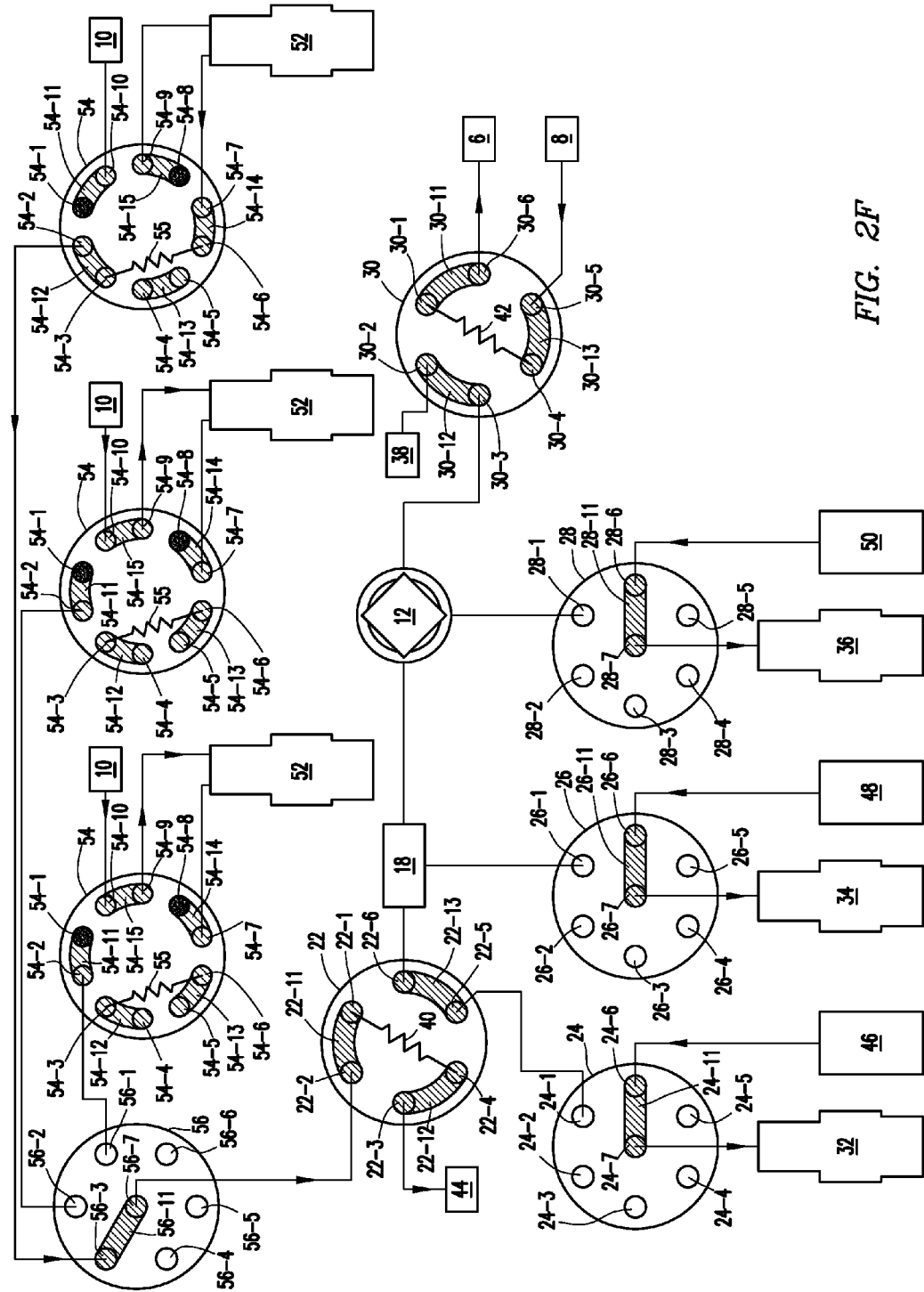
FIG. 2F shows the automated sampling and reaction system configured to collect sample from multiple non-pressurized sample sources.

As shown in FIG. 2B, FIG. 2C and FIG. 2F, the automated sampling and reaction system 2 can include one or more external auxiliary sampling valves 54 and one or more external sample pumps 52 combined in a way that allows sampling from one or more non-pressurized supply of sample such as a reactor or reactor stream 10 or dissolution bath (not shown). The automated sampling and reaction system 2 can be used to draw a plurality of process samples from a single source of sample or, with the use of a selection valve 56, a plurality (more than one) of reactors 10 or dissolution baths or other sources of sample.

As shown in the figures, the external auxiliary sampling valve 54 has ten fluidic ports 54-1, 54-2, 54-3, 54-4, 54-5, 54-6, 54-7, 54-8, 54-9, and 54-10 and five flow-through conduits 54-11, 54-12, 54-13, 54-14, and 54-15. Fluidic ports 54-1 and 54-8 are plugged and not used for fluid flow of sample. A third sample loop 55 connects fluidic ports 54-3 and 54-6. Tubing connects the external auxiliary sampling valve 54 to the reactor 10 and to the external sample pump 52. Tubing also connects the external auxiliary sampling valve 54 to the external sampling valve 22. More specifically, tubing connects fluidic port 54-10 to the non-pressurized reactor 10. Tubing further connects fluidic ports 54-7 and 54-9 to the external sample pump 52. In addition, tubing connects the fluidic port 54-2 to the fluidic port 22-2 of the external sampling valve 22.

The external sample pump 52 is a positive displacement pump. During startup, a liquid positive displacement pump cannot simply draw air until the feed line and pump fill with the liquid that requires pumping. Typically, an operator must introduce liquid into the system to initiate the pumping. While loss of prime is usually due to ingestion of air into the pump, the clearances and displacement ratios in pumps for liquids and other more viscous fluids usually cannot displace air due to its higher compressibility.

The selection valve 56 has seven fluidic ports 56-1, 56-2, 56-3, 56-4, 56-5, 56-6 and 56-7 and one flow-through conduit 56-11. The number of selection valves 56 depends, in part, on the number of external auxiliary sampling valves 54. It is optional for the automated sampling and reaction system 2 to include one or more selection valves 56 with only one external auxiliary sampling valve 54. However, the automated sampling and reaction system 2 having a plurality of external auxiliary sampling valves 54 requires one or more selection valves 56.

When samples are drawn from a plurality of reactors 10, there is at least one external auxiliary sampling valve 54 in fluidic communication with each reactor 10. Furthermore, when the automated sampling and reaction system 2 has two or more external auxiliary sampling valves 54, at least one selection valve 56 is required. In other words, while a plurality of external auxiliary sampling valves 54 and/or a plurality of selection valves 56 could be connected to a single reactor 10, at least one selection valve 56 must be provided for the automated sampling and reaction system 2 having two or more external auxiliary sampling valves 54. For the automated sampling and reaction system 2 having a plurality of external auxiliary sampling valves 54, tubing connects fluidic port 54-2 of each external auxiliary sampling valve 54 to the selection valve 56. Fluidic port 54-2 can be connected to any of fluidic ports 56-1, 56-2, 56-3, 56-4, 56-5 or 56-6 of the selection valve 56 and in alternative combinations.

More specifically, as shown in FIGS. 2B, 2C and 2F, tubing connects fluidic ports 54-7 and 54-9 of the external auxiliary sampling valve 54 to the external pump 52. Tubing connects fluidic port 54-10 of the external auxiliary sampling valve 54 to the reactor 10 or other source of sample. Tubing connects fluidic ports 54-2 of the external auxiliary sampling valve 54 to fluidic port 22-2 of the external sampling valve 22 when a single external auxiliary sampling valve 54 is used (FIGS. 2B and 2C). Where a plurality of external auxiliary valves 54 are used, tubing can connect fluidic port 54-2 of the external auxiliary valve 54 to each of fluidic port 56-1, 56-2, 56-3, 56-4, 56-5 or 56-6 of the selection valve 56 (FIG. 2F).

FIG. 2F depicts an example of the automated sampling and reaction system 2 having three external auxiliary sampling valves 54 and one selection valves 56. Fluidic port 56-7 of each selection valve 56 is connected to the external sampling valve 22. Fluidic port 54-2 of each external auxiliary sampling valve 54 is connected to the selection valve 56 at fluidic ports 56-1, 56-2 and 56-3. As shown, fluidic port 56-7 of the selection valves 56 is connected to fluidic port 22-2 of the external sampling valve 22.

The various combinations of valve configurations for the selection valve 56 and the external auxiliary sampling valves 54 effectively determines the fluidic pathway from the reactor 10, the external auxiliary sampling valve 54, and the selection valve 56 to the external sampling valve 22. In short, the configuration of the selection valve 56 determines the fluidic pathway of sample from which reactor 10 to the external sampling valve 22. Clockwise and counterclockwise rotation of the external auxiliary sampling valve 54 achieves the same configuration. Optionally, the selection valve 56 can have eight fluidic ports with a flow-through conduit (not shown).

Sample Collection from a Single Non-Pressurized Sample Source

As described immediately above, the automated sampling and reaction system 2 can be configured to draw a sample from a non-pressurized sample source. As described herein, the external auxiliary sampling valve 54 can toggle between two configurations, the first configuration and the second configuration, to perform three steps: draw sample, load sample into the third sample loop 55 and discharge sample. In the first configuration shown in FIG. 2B, the external sample pump 52 draws sample from the reactor 10. In the second configuration shown in FIG. 2C, the external sample pump 52 discharges sample into the third sample loop 55 of the external auxiliary sampling valve 55. Returning to the first configuration of the external auxiliary sampling valve 54, the external sample pump 52 discharges sample from the third sample loop 55 to the external sampling valve 22.

More specifically, as shown in FIG. 2B, in the first configuration, the external sample pump 52 draws sample from the reactor 10 through fluidic port 54-10 of the external auxiliary sampling valve 54 into flow-through conduit 54-15 and out fluidic port 54-9 to the external sample pump 52. As shown in FIG. 2C, in the second configuration, the external auxiliary sampling valve 54 has been rotated one port position clockwise or counterclockwise. In this second configuration, the external sample pump 52 discharges sample into fluidic port 54-7 of the external auxiliary sampling valve 54 through flow-through conduit 54-14 and out fluidic port 54-6 through the third sample loop 55 and then into fluidic port 54-3 through flow-through conduit 54-12 and out fluidic port 54-2 to the fluidic port 22-2 of the external sampling valve 22 and continuing through fluidic conduit 22-11 and out fluidic port 22-1 to load sample into the first sample loop 40 of the external sampling valve 22.

The external auxiliary sampling valve 54 then rotates counterclockwise toggling back to the first configuration. The external sample pump 52 displaces sample drawn through the third sampling loop 55. The sample pump 32 discharges wash to external sampling valve 22 as described immediately below in FIGS. 3 through 7. If the configuration of the external sampling valve 22 is not changed and remains as described in FIG. 2, the sample will be discharged into the collection reservoir 44, provided the external sample pump 52 is turned on.

Alternatively, the external sampling valve 22 may be replaced with the external auxiliary sampling valve 54, as shown in FIGS. 2D and 2E. Here, the fluidic ports 54-2 and 54-5 of the external auxiliary sampling valve 54 are plugged and not used for sample flow. Fluidic ports 54-1 and 54-8 are not plugged. As shown in FIGS. 2D and 2F, tubing connects fluidic ports 54-4 and 54-6 of the external auxiliary sampling valve 54 to the external pump 52. Tubing connects fluidic ports 54-1 and 54-3 of the external auxiliary sampling valve 54 to the reactor 10 or other source of sample. Tubing connects fluidic port 54-8 of the external auxiliary sampling valve 54 to fluidic port 24-1 of the priming valve 24. Tubing further connects fluidic port 54-9 of the external auxiliary sampling valve 54 to the mixing tee 18.

FIGS. 2D and 2E each show the first and the second configurations of external auxiliary sampling valve 54, respectively. As shown in FIG. 2D, in the first configuration, sample is drawn from the reactor 10 through fluidic port 54-3, into flow-through conduit 54-12 and out fluidic port 54-4 to the external sample pump 52. As shown in FIG. 2E, in the second configuration, the external sample pump 52 discharges sample into fluidic port 54-6 of the external auxiliary valve 54 through flow-through conduit 54-14 and out fluidic port 54-7 filling the third sample loop 55 into fluidic port 54-10 through flow-through conduit 54-11 and out fluidic port 54-1 recirculating back to the reactor 10. Sample constantly flows through the third sample loop 55 in this manner. The external auxiliary sampling valve 54 then rotates counterclockwise toggling back to the first configuration.

Sample Collection from Multiple Non-Pressurized Sample Sources

Samples can be taken from one or more non-pressurized sources (reactors, reactor flow streams, and the like) sequentially or simultaneously, in series or in parallel. Each external auxiliary sampling valve 54 draws sample independently from the other. However, the number of samples that can be taken depends on the number of external auxiliary sampling valves 54 provided in the automated sampling and reaction system 2. Also, for each external auxiliary sampling valve 54, an external sample pump 52 is provided. Further, if a plurality of external auxiliary sampling valves 54 is required, there must be one selection valve 56 and there can be up to six external auxiliary sampling valves 54 for every one selection valve 56.

To draw sample from multiple reactors 10 or other sources, the external sample pump 52 must be on. As described above, the external auxiliary sampling valves 54 alternate between two configurations and do so, in three steps. Each of the external auxiliary sampling valves 54 can be in the same configuration or can be in the other configuration, i.e., the first configuration versus the second configuration described above.

By way of example, FIG. 2F shows automated sampling and reaction system 2 having three external auxiliary sampling valves 54 and one selection valve 56. As shown in FIG. 2F, the external auxiliary sampling valves 54 can be in different configurations. In this example, sample can be drawn from the reactor 10 through fluidic port 54-10 into flow-through conduit 54-15 and out fluidic port 54-9 of the external auxiliary sampling valve 54. Concurrently, sample could be displaced in the third sample loop 55 of another external auxiliary sampling valve 54 and discharged to selection valve 56.

Sample Collection from Multiple Pressurized Sample Sources

Figure 2G:
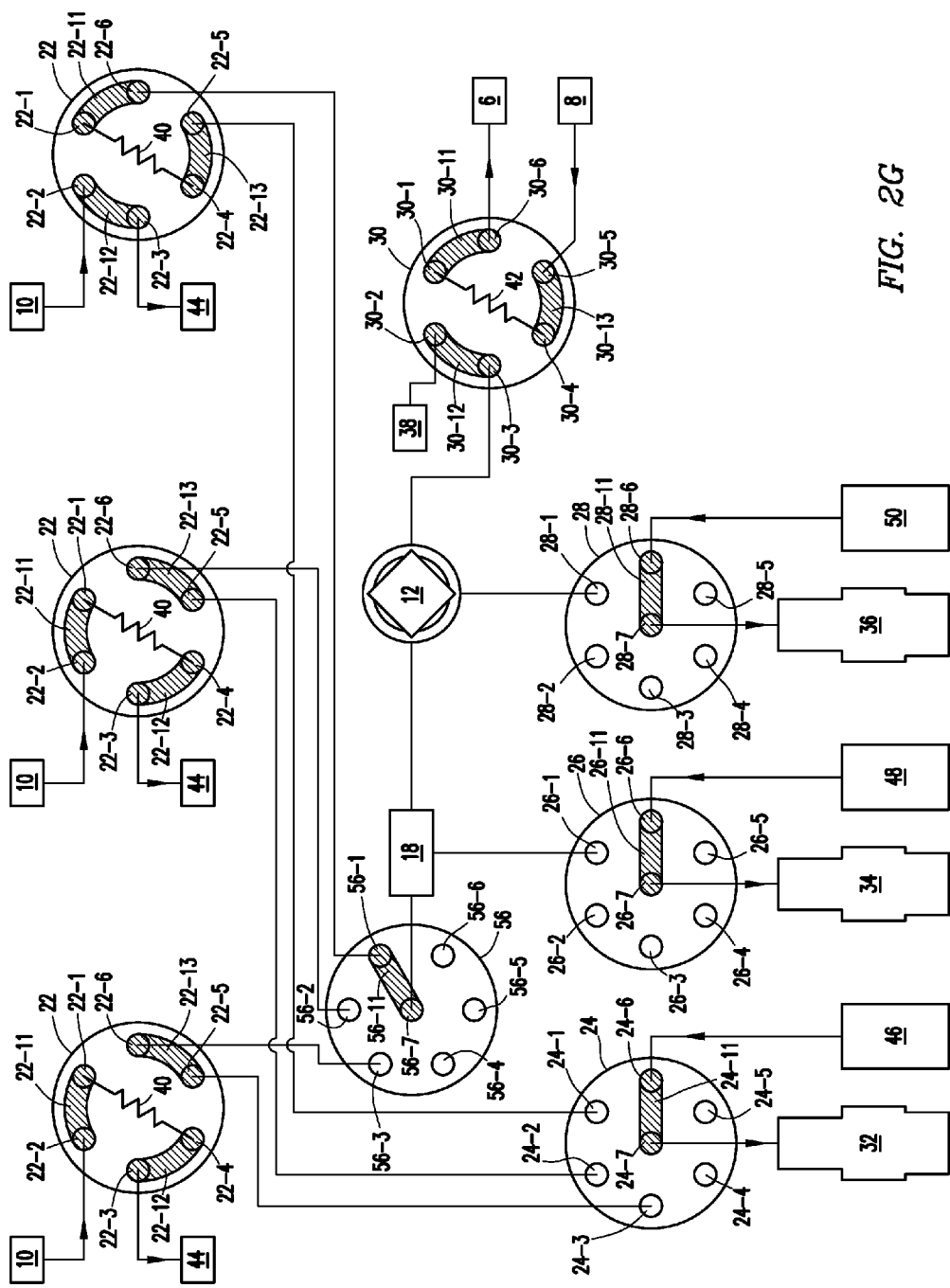
FIG. 2G shows the automated sampling and reaction system configured to collect sample from multiple pressurized sample sources.

The automated sampling and reaction system 2 can be configured to draw samples from more than one source of sample under pressure, in sequence or in parallel. As shown in FIG. 2G, to draw sample from multiple sample sources under pressure, the automated sampling and reaction system 2 can include a plurality of external sampling valves 22 and at least one selection valves 56. The external sampling valves 22 and selection valve(s) 56 are combined in a way that allows sampling from one or more pressurized supply of sample such as a reactor 10 or reactor stream or dissolution bath (not shown), or other sources of sample. The number of selection valves 56 depends, in part, on the number of the external sampling valves 22. However, at least one selection valve 56 must be present when five or less external sampling valves 22 are used.

FIG. 2G depicts an example of the automated sampling and reaction system 2 comprising three external sampling valves 22 and one selection valve 56. As described herein, each external sampling valve 22 has six fluidic ports 22-1, 22-2, 22-3, 22-4, 22-5 and 22-6 and three flow-through conduits 22-11, 22-12 and 22-13. The first sample loop 40 connects fluidic ports 22-1 and 22-4. As shown, tubing connects fluidic port 22-2 of each of the external sampling valves 22 to the reactor 10, and fluidic port 22-3 to the collection reservoir 44. Tubing further connects fluidic port 22-5 of each external sampling valve 22 to fluidic ports 24-1, 24-2 and 24-3 of the priming valve 24 and fluidic port 22-6 of each external sampling valve 22 to fluidic ports 56-1, 56-2 and 56-3 of the selection valve 56. Fluidic port 22-5 can be connected to any of the fluidic ports 24-1, 24-2, 24-3, 24-5 or 24-6 of the priming valve 24 and in alternative combinations. However, at least one fluidic port of the priming valve 24 must be connected to the wash reservoir 46. Fluidic port 24-7 is then connected to the sample pump 32. Similarly, fluidic port 22-6 can be connected to any of the fluidic ports 56-1, 56-2, 56-3, 56-4, 56-5 or 56-6 and in alternative combinations. Tubing also connects fluidic port 56-7 to the mixing tee 18.

The combination of the first and second configurations of the external sampling valve, together with the configurations of the selection valve 56 and the priming valve 24, effectively determine the fluidic pathway from the reactor 10 to the mixing tee 18. For example, as shown in FIG. 2G, two external sampling valves 22 are shown in the first configuration providing a fluidic pathway between the reactor 10 and the collection reservoir 44. The other external sampling valve 22 is in the second configuration, providing a fluidic pathway between the reactor 10 and the mixing tee 18.

Sample Dilution

FIG. 3 shows the automated sampling and reaction system 2 configured to dilute (or quench) sample at the mixing tee 18. As shown, the configurations of the priming valve 24, the external sampling valve 22 and the diluent valve 26 are changed from those shown in FIG. 2 so that sample and diluent are discharged into the mixing tee 18.

Specifically, in its second configuration, the priming valve 24 is rotated counterclockwise by one port position such that the flow-through conduit 24-11 connects fluidic port 24-7 to fluidic port 24-1 to establish a fluidic pathway between the sample pump 32, the priming valve 24 and the external sampling valve 22. Likewise, in its second configuration, the external sampling valve 22 is rotated clockwise by one port position such that the flow-through conduit 22-11 connects fluidic port 22-1 to fluidic port 22-6, establishing a fluidic pathway between the first sample loop 40 and the mixing tee 18. In addition, the flow-through conduit 22-13 connects fluidic port 22-5 to fluidic port 22-4 such that a fluidic pathway is established between the priming valve 24 and the mixing tee 18. Counterclockwise rotation of the external sampling valve 22 by one port position achieves the same configuration. Also, in its second configuration, the diluent valve 26 is rotated counterclockwise one port position such that flow-through conduit 26-11 connects fluidic port 26-1 to fluidic port 26-7 establishing a fluidic pathway between the diluent pump 34 and the mixing tee 18.

In short, for sample dilution, sample is discharged from the first sample loop 40 of the external sampling valve 22 through fluidic port 22-1 into flow-through conduit 22-11 and out fluidic port 22-6 to the mixing tee 18. Simultaneously, the dilute pump 34 discharges diluent from the diluent valve 26 through fluidic port 26-7 into flow-through conduit 26-11 and out fluidic port 26-1 to the mixing tee 18. Sample is mixed with diluent and diluted at the mixing tee 18. For sample dilution, the sample pump 32 and the diluent pump 34 must discharge sample and diluent concurrently to the mixing tee 18. The flow rates of the pumps 32 and 34 determine the dilution ratio (overall dilution flow rate to process sample flow rate). Consider, for example, an overall dilution flow rate of 100 µl/min, with the sample pump 32 discharging 10 µl/min of sample while the diluent pump 34 discharges 90 µl/min of diluent: the result is a 10:1 dilution. When, for example, the sample pump 32 pushes 50 µl/min, while the diluent pump 34 pushes 50 µl/min, the result is a 2:1 dilution. Furthermore, the timing of the system is such if sample is retained in the mixing tee 18 too long, sample may get diffused. So, sample should be diluted as soon as possible. Moreover, by diluting sample as it is moved through the mixing tee 18, a larger volume is created and the sample can be moved greater distances.

Before or during sample dilution, the configuration of the reagent valve 28 can change to a second configuration, by rotating counterclockwise by one port position such that the flow-through conduit 28-11 connects fluidic port 28-1 to fluidic port 28-7. In this configuration, the reagent pump 36 discharges reagent through fluidic port 28-7 through flow-through conduit 28-11 and out fluidic port 28-1 to the microreactor 12. However, the reagent valve 28 does not have to change at the same time that the configurations of the external sampling valve 24 and the priming valve 26 or before the sample preparation step.

As noted above, sample can be drawn from a reactor or reactor flow stream operating under pressure or under non-pressurized reaction where the reactor or other vessel is not operating under pressure (i.e., at a pressure greater than about 1 atmosphere or 14.7 psi at sea level). The system 2 described herein can dilute a sample drawn from the reactor by diluting sample at the mixing tee 18 (also sometimes referred to as direct dilution line load). Alternatively, the system 2 can provide a direct sample load to the injection valve 30 via the microreactor 12 without sample dilution.

Sample Preparation

FIG. 4 depicts the automated sampling and reaction flow system 2 having valves configured to add reagent or other reactants to sample in the microreactor 12. The configurations of the priming valve 24, the external sampling valve 22 and the diluent valve 26 remain as immediately described above in the dilution step and as shown in FIG. 3. At this time, the reagent valve 28 is configured in a second configuration such that flow-through conduit 28-11 connects fluidic port 28-1 to fluidic port 28-7 and provides a fluidic pathway between the reagent pump 36 and the microreactor 12. Reagent pump 26 discharges reagent and/or other reactants into fluidic port 28-7 through flow-through conduit 28-11 and out fluidic port 28-1 to the microreactor 12.

As demonstrated in FIG. 4, diluted sample flows from the mixing tee 18 to the microreactor 12, as illustrated by arrows. The microreactor 12 is set to operate at the proper temperature, pressure and time for sample to react with the reagent or other reactants, and to permit the reaction to go to completion. Essentially, diluted or un-diluted sample and reagent are provided to the microreactor 12 at a specific rate to ensure that proper ratios of both are maintained. Sample and/or reagent can be discharged through the injection valve 30 via the second sample loop 42 to the waste reservoir 38.

Furthermore, during sample preparation, the sample pump 32, the diluent pump 34 and the reagent pump 36 are preferably turned on. Alternatively, during sample preparation, either sample pump 32 or the diluent pump 34 can be turned off provided the other remains on. For example, if the sample pump 32 is turned off, the configuration of the priming valve 24 is changed by rotating clockwise one position and external sampling valve 22 is changed by rotating one position either counterclockwise or clockwise. On the other hand, if the dilute pump 34 is turned off and the sample pump 32 remains on, the configuration of the dilute valve 26 changes by rotating the clockwise one position.

Microreactors

Microreactors are small scale, continuous flow reactors. Microreactors are also sometimes referred to as microstructured devices or microchannel devices. In the microreactor, chemical reactions go forward in a confined environment and over wide ranges of temperature and pressure, each of which can be optimized according to the user's preferences to ensure completion of the specified chemical reaction. Microreactors can be manufactured from a range of materials that include, but are not limited to, glass, silicon-glass, ceramic, stainless steel or polymers.

There are different types of microreactors including, but are not limited to, chip, capillary, microstructured and industrial microreactors. The microchannel design includes a mesh, catalyst-trap, micro-packed bed, falling film, and/or meandering channels. Microreactors can include mixing units, flow distributors, multiple channels, and means for immobilizing catalyst particles. They can also have a variety of channel geometries, diverse mixing and heat exchange structures. See, e.g., Jensen K. F., Reizman B. J., Newman S. G., *Tools for Chemical Synthesis in Microsystems*, May, 2014 at pp. 1-2. For example, the mixing units, or micromixers, made of glass with variability in outlet geometries, such as triangular-shaped, heart-shaped, linear and so on, allow the visual investigation of the mixing process and the generation of emulsions.

Generally, microreactors can have channels with diameter ranges between sub-mm to tens of mm range and can have surface to volume ratios from about 1,000 to more than about 50,000 $m^2/m^3$. For example, the gas-liquid types of microreactors include, but are not limited to, the following examples of microreactors: micro bubble column microreactors (1100 μm×170 μm channel size) have an interface area of about 5,100 $m^2/m^3$, micro bubble column microreactors (300 μm×100 μm channel size) have an interface area of about 9,800 $m^2/m^3$, micro bubble column microreactors (50 μm×50 μm channel size) have an interface area of about 14,800 $m^2/m^3$ and falling film microreactors (300 μm×100 μm channel size) have an interface area of about 27,000 $m^2/m^3$.

In a microreactor, sample and reagent streams are continuously pumped into the microreactor. Reactants can be mixed and reacted in the microreactor. The reaction product can leave the microreactor as a continuous stream. Walls of microchannels typically have high heat transfer coefficient of at least about 1 MW per $m^3$ per K, enabling heat removal more efficiently and allowing critical reactions to be performed safely at high temperatures, such as for example nitration reactions. Flow capabilities of microreactors range from about 0.45 ml to about 260 ml per single plate per minute and throughput of microreactors can range from about 2 g/min to about 4500 g/min, or up to hundreds of kg/hr. For example, in the liquid-liquid capillary microreactors with slug, bubbly, parallel and annular flow hydrodynamics, the flow rate is directly dependent on capillary length and aqueous-to-organic volumetric flow ratio. See, e.g, van Duijn, C. J. *Liquid-Liquid Microreactors for Phase Transfer Catalysis*, December, 2011, Chapter 2, pp 25-26. Additionally, certain industrial microreactors can operate at high pressures of up to 600 bar in stainless steel microreactors.

Microreactors are used for a variety of chemical reactions and can be used in many industries that include but not limited to pharmaceutical, chemical, petrochemical and petroleum fields. The most common types of derivatization include the addition of a chromophore or fluorescent functional group. Other examples of common notable reactions include but not limited to Friedel-Crafts alkylation, ester hydrolysis, oxidations, phase transfer catalysis, emulsion polymerization, fluorination of tulene, ammonia oxidation, aromatic nitration, ethane epoxidation, and dehydration of methanol to form formaldehyde. For instance, nitration of aromates with dinitrogen pentoxide is a liquid phase reaction with a fast reaction time of less than 10 seconds and must be performed at temperatures below 50° C., requiring extensive cooling capabilities. In addition, this reaction is highly exothermic (−500 kJ/mol). Generally, sample components with active functional such as, but not limited to, alcohols, phenolic, amine, carboxyl, olefin, and others, are candidates for derivatization.

Furthermore, microreactors can be used for derivatization chemistry for analysis of a broad range of samples that contain a suitable active functional group (or groups) available for derivatization (or chemical reaction) such as polar groups (amines). Derivatization includes a chemical reaction between an analyte and a reagent to change the chemical and physical properties of the analyte. Advantages of derivatization include improved detectability, change in molecular structure of analyte for better chromatography, increase volatility, change the matrix for better separation and stabilization an analyte. Ideally, derivatization reactions should be rapid, quantitative and produce minimal by-products. Excess reagent should not interfere with the analysis can should be easily removed.

For example, Waters AccQTag method is a precolumn derivatization technique for peptide and protein hydrolysate amino acids. The AccQTag Amino Acid Analysis method can utilize a derivatizing reagent, such as AccQFluor reagent 6-aminoquinolyl-N-hydroxysuccinimidyl carbamate ("AQC"), which forms stable derivatives with primary and secondary amino acids in a matter of seconds, with the microreactor providing proper temperature and pressure conditions. See, e.g., EP 0 533 200 B1 at paragraphs [0011], [0020], [0021], [0023], [0026] and [0034], incorporated by reference as well as the entire contents and teachings of which are incorporated herein by reference. The amino acid derivatives can then be injected directly into the column without further preparation. The amino acid derivatives can then be injected directly into the column without further preparation.

Other useful reagents include, but are not limited to, molecules used to rapidly label molecules in a sample in order to improve detectability for subsequent analysis by liquid chromatography, mass spectrometry, fluorescence and ultra-violet detection. See, e.g., WO2013/049622 at page 2, lines 11 through page 3, line 20; page 9, line 14 through page 13, line 2; page 22, line 23 through page 30, line 20; and page 32, line 15, incorporated by reference as well as the entire contents and teachings of which are incorporated herein by reference. Here, the MS active, fluorescent molecules are useful as reagents for rapid tagging of glycans such as N-linked glycans and other bio-molecules such as proteins and peptides and amino acids. These MS active, fluorescent molecules can have three functional components: (a) a tertiary amino group or other MS active atom; (b) a highly fluorescent moiety, and (c) a functional group that rapidly reacts with amines, such as an isocynanate or succidimidylcarbamate. The reactive functional group provides rapid tagging of desired bio-molecules, and the fluorescent moiety provides for a strong fluorescent signal. The tertiary amino group substituent provides a strong MS signal. In another aspect, these rapid tagging MS active compounds do not have to have a fluorescent moiety.

There are many advantages to using microreactors as most chemical reactions generally benefit from a continuous process where solids are not present. For example, microreactors provide high surface-to-volume ratio which allows for enhanced mass and heat transfer and eliminates reaction hot spots. Rapid heat transfer allows increased contact between molecules of the reactants, such as between the sample and the derivatization reagent, for a sufficient enough time to allow a reaction to go to completion. In other words, due to small surface-to-volume ratios that enable microreactors to absorb heat created from a reaction much more efficiently. Local temperature gradients that affect reaction rates are much smaller in the microreactors which allows for better kinetic investigations. In addition, heating and cooling a microreactor is much quicker than traditional vessels used for chemical reactions, allowing very low operating costs. The superior heat exchange, heat transfer and cooling capabilities are maintained by sandwiching a thin reaction layer between cooling plates and increasing lateral size while keeping a constant reactor channel depth.

In addition, microreactors provide laminar flow conditions, uniform residence time of the sample and reagent molecules, have high-throughput with minimal amounts of sample used, low manufacturing, operating and maintenance costs. Furthermore, when a larger amount of product is desired, the use of microreactors allows for seamless transfer of favorable mass and heat transfer conditions established on a smaller research scale to industrial scaled-up manufacturing. Thus, scale-up is typically achieved by increasing reactor size while preserving heat and mass transfer advantages, and then multiplying up the resulting smaller number of larger reactors.

Microreactors are available for small-scale and commercial use. Microreactors range from smaller devices with lateral dimensions below about 1 mm to scaled-up commercial microreactors for industrial chemical production setups. For seamless scale-up, modular microreaction systems are usually employed. Microreactors can include a single module capable of supporting mixing, heat exchange and reaction simultaneously. Alternatively, microreactors can include one or more mixing modules, heat exchange modules and/or reaction modules. Generally, at the point of scale-up, a module with more channels is employed assuring identical process results between the pilot, or discovery process and the production stage, as the physical condition in each channel remains the same.

For example, during the discovery process, results can be measured in µg to mg. With an automated flow chemistry platform for rapid reaction screening, the type of microreactor that can be employed could have a 300 µm channel width such as in the Labtrix® System, for example currently sold by Chemtrix. Such systems can include scouting and optimization, kinetic data generation, process feasibility studies, process validation and additive screening. These systems can perform syntheses at temperatures between about −20° C. to about 195° C. and at pressures up to about 25 bar. The system can evaluate many reaction parameters in a short period of time with very little raw material.

For the development stage, modular scalable flow reactor systems such as the KiloFlow® system currently sold by Chemtrix can be used to support reaction development up to Phase 3 within a standard fume hood and without re-optimization or change in mixing efficiency. These systems can perform syntheses at temperatures between about −15 and about 150° C. having reaction times in the range of about 1.0 second to about 100 minutes. Production capabilities range between about about 10 to about 6000 milliliters per hour. Each module can have static mixers in the range of about 60 to about 250 ms and a thermal regulator which enables the use of process parameters in the discovery stage to provide the same results on a gram to kilogram scale where a single channel or parallel channel reactor are used. Furthermore, syringe pumps can be selected for high precision dosing of reagent solutions at high pressure (maximum operating pressure at about 20 bar). To allow for continuous dosing of reagents to the reactor, the pumps can be operated as dual syringe pumps, for example, with four pump units used to deliver two reagent solutions in the system. Using software, synchronized control over all dosing units can be achieved to allow access of flow rates of about 0.1 to about 50 min—1 per reagent feed (using 25 ml syringes) for example. Single dosing is also possible over the range about 0.01 to about 50 milliliters (ml)—1 using 25 ml syringes. In addition, reagents can be pre-heated before transferring to a reactor module where they are mixed. The heat exchangers can be thermally regulated using a closed recirculating thermostat. Within the system, heat exchange modules sometimes have two functions: (1) to thermostat reagent feeds and (2) bring reaction product stream to ambient temperature ahead of sample collection.

For production, industrial flow reactors can execute hundreds of reactions per day and allow high production volumes in flow, producing at the ton-scale for the execution of highly profitable processes. For example, Plantrix® industrial flow reactor currently sold by Chemtrix is a modular reactor that allows high production volumes in flow and can produce at the ton-scale. Because this type of reactor is a modular reactor, there is less scale-up risk associated with its use. The different reactor modules can be installed, enabling the system to be tailored to a specific process by varying mixing time, residence time and quench. Plantrix® reactors can handle volumes from about 2.9 ml to about 5 L per reactor system and have temperature resistance up to about 1500° C., with thermal conductivity five times higher than stainless steel. In addition, using millimeter channel dimensions, these reactors can tolerate the use of solids in the process stream up to about 100 µm in size. Furthermore, Plantrix® reactors can be used for a wide range of chemical process including very challenging reactions, such as, but not limited to, fast exothermic reactions, reactions with aggressive media, reactions employing unstable intermediates, hazardous reactions, and are suitable for both acidic and alkaline materials.

Sample Loading

FIG. 5 shows the automated sampling and reaction system 2 having valves configured to load sample into the second sample loop 42 of the injection valve 30. The configuration of the external sampling valve 22, the priming valve 24, the diluent valve 26 and the reagent valve 28 remain as shown in FIG. 4. However, the configuration of the injection valve 30 is changed to a second configuration. The injection valve 30 is rotated clockwise by one port position. Rotation of the injection valve 30 counterclockwise by one port position achieves the same configuration. The sample pump 32, the diluent pump 34 and the reagent pump 36 are turned to discharge sample into second sample loop 42 of the injection valve 30, as illustrated by arrows. Specifically, in this configuration, flow-through conduit 30-12 of the injection valve 30 provides a fluidic pathway from the microreactor 12 into fluidic port 30-3 of the injection valve 30 and out fluidic port 30-4 through the second sample loop 42 into fluidic port 30-1 through flow-through conduit 30-12 and out fluidic port 30-2 to the waste reservoir 38.

Sample Injection

FIG. 6 shows the automated sampling and reaction system 2 having valves configured to inject sample into the column 6. The configurations of the external sampling valve 22, the priming valve 24, the diluent valve 26, the reagent valve 28 and the injection valve 30 change from the loading step immediately described above.

To introduce the diluted and derivatized sample to the solvent composition stream, the injection valve 30 is rotated counterclockwise by one port position back to a first configuration such that the flow-through conduit 30-11 connects fluidic port 30-1 to fluidic port 30-6 to provide a fluidic pathway from the second sample loop to the column 6 or detector (not shown). In addition, the flow-through conduit 30-13 connects fluidic port 30-4 to fluidic port 30-5 to provide a fluidic pathway from the solvent delivery system 8 to the second sample loop 42. Clockwise rotation of the valve 30 by one port position will achieve the same configuration. Sample contained therein in the second sample loop 42 is introduced into solvent composition stream arriving from the solvent delivery system 8.

In addition, the external sampling valve 22, the priming valve 24, the diluent valve 26 and the reagent valve 28 can optionally remain in the configuration as shown in FIG. 5 but preferably change to configurations in the collection step and as shown in FIG. 2. More specifically, the external sampling valve 22 is rotated counterclockwise by one port position (clockwise rotation by one port position achieves the same configuration). As described above, this configuration provides a fluidic pathway between the reactor 10 and the collection reservoir 44 via the external sampling valve 22 through the first sample loop 40.

Similarly, the priming valve 24, the diluent valve 26 and the reagent valve 28 can optionally remain in the configurations as shown in FIG. 5 but preferably are changed to the configurations as shown in FIG. 2. Each of the valves rotates independent of the other clockwise by one port position. In addition, the sample pump 32, the diluent pump 34 and the reagent pump 36 can be turned off during the injection step. However, for speed of sampling and preparation, the sample pump 32, the diluent pump 34 and the reagent pump 36 remain on to be refilled and ready for the next injection as shown in FIG. 2.

Example 1

Chemistry of AQC Derivatization

AccQTag derivatization reaction is appropriate for the systems and methods described herein. For example, AccQTag derivatization has been in use for over 10 years. See e.g., EP0533200 B1 at paragraphs [0011], [0020], [0021], [0023], [0026] and [0034], incorporated herein by reference. Here, a reagent reacts with non-protonated primary and secondary amino acids in a largely aqueous environment to form products that are readily detected by a UV detector. Since the same group is being added to each of the amino acids, the extinction coefficients of the derivatized amino acids are very much the same. In other words, the responses for equimolar amounts of the amino acids are very similar. The complete chemistry occurring in the reaction tube is shown immediately below.

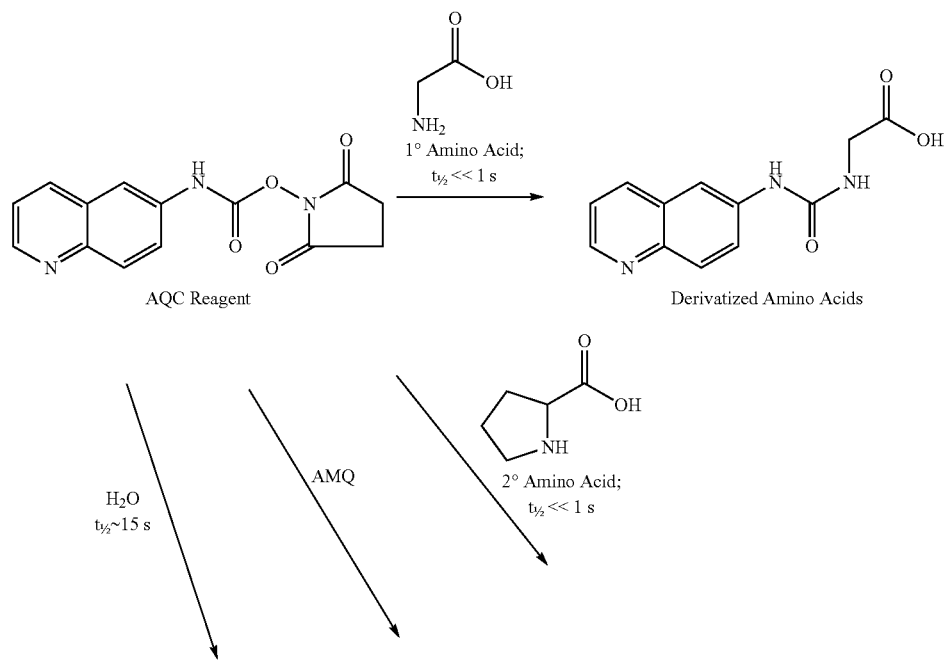

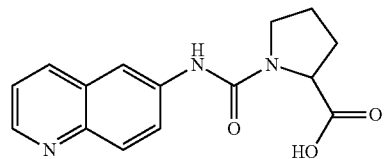

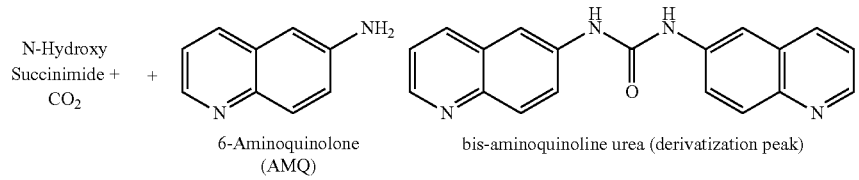

As shown, the primary and secondary amino acids undergo reaction with the reagent on a time scale of tens of milliseconds and is therefore complete in less than about 1 second. The excess reagent then reacts with water on a time scale of 10 s of seconds and forms byproducts that do not interfere with the amino acid analysis, for example. No special handling is required to remove the excess reagent and the reaction may be carried out on the bench top.

Example 2

Manual Derivatization of Amino Acids Using AccQTag Kit

Unlike systems and methods described herein, the following scheme is exemplary of steps taken in manual derivatization of sample containing amino acids. This methodology is presented in contrast to the automated sampling and reaction system and associated methods described herein. First, reagent is reconstituted using 3×1 mL rinse of pipette tip with diluent. The reagent vial is tapped on the table to assure material is at the bottom of the vial. 1 mL of reagent diluent is transferred to the reagent vial and vortex the vial and placed atop a heatblock set to 55 C for ten minutes. As provided in Table 1, borate buffer is then added to blanks, standard sample and sample and any necessary base volumes to Waters Total Recovery Vial and vortex to mix thoroughly. For example, 20 µL of reconstituted reagent is added below liquid level in TRV to each vial, then capped and vortex immediately. The vial is allowed to stand at room temperature for one minute, then placed in 55° C. heat block for 10 minutes. As described herein, these steps can now be performed in the microreactor and automatically.

TABLE 1

| Volumes (µL) | Gradient Blank | Derivatization (Reagent) Blank | Standard, Sample |
|---|---|---|---|
| AccQ•Tag Ultra Borate Buffer | 80 | 80 | *70 |
| AccQ•Tag Ultra Reagent Diluent | 20 | | |
| Standard or Sample | | | 10 |
| NaOH for neutralizing sample | | | * |
| reconstituted AccQ•Tag Ultra Reagent | | 20 | 20 |

Some guidelines should be followed for successful derivatization. First, the amount of sample present needs to be within the dynamic linear range of the method and above likely environmental contaminant levels (>1 picomole on column for least abundant amino acid (LAAA) and <140 nanomol of total amines in the derivatization cocktail. Second, pH should be between 8 and 10, to assure amines are unprotonated. Borate volume in the derivatization needs to be sufficient to neutralize 0.1 N acid. For samples with more than 0.1N acid, adjust with equal volume of base at the same concentration. The pH must not be so low or so high that the reagent is destroyed. Third, there must be sufficient excess of reagent to drive the derivatization reaction to completion. For example, ~5× molar excess of reagent over sample is required.

Other considerations for successful quantitative analysis of amino acids include, first, the organic concentration of the derivatization mixture must be high enough to keep the reagent and the derivatives in solution but not so high as to distort the chromatography. Second, the amino acid concentration must be above the required sensitivity limits. Third, the sample must not be contaminated with amino acids, with proteins, or with other environmental amines.

Furthermore, data should be reviewed to confirm that there are no significant peaks in the gradient blank and verify that the AMQ peak height is ≥0.9 AU for all derivatized samples. The reagent blank chromatogram should not have significant amino acid contamination (≤50 femtomoles, Gly ≤100 femtomoles) and multiple injections of the standard should overlay well. Mono-derivatized lysine should not exceed 2% of Phe height. Also, retention time alignment of amino acid peaks should be compared with component markers and adjusted.

To troubleshoot poor quantitation, one should consider that hydrophobic amino acids come out of solution if not enough organics are present. If there are too many organics in derivatization, this will distort early eluting peaks. Furthermore, evaporation of organic in the secondary sample can also result disproportionately larger early peaks and smaller later peaks. As to derivatization-related quantification, the AMQ peak size should be ≥0.90 AU. Furthermore, Asp, Glu, Lys, Ala are most sensitive to pH and not enough excess reagent. Moreover, Ala/Phe ratio of the standard can indicate if the reagent is bad or if there is a problem with the Borate buffer and the presence of mono-derivatized Lysine indicates incomplete derivatization. Also, certain quantitation problems are hydrolysis-related including: (1) methionine recovery varies with oxygen exposure; (2) tyrosine, threonine, and serine are gradually destroyed; (3) hydrophobics may be released slowly; (4) too much solids or not enough acid slows or stops hydrolysis; and (5) protein or amino acid contamination introduced.

Therefore, for troubleshooting, identifying obvious issues such as instrumentation, chemistry or sampling problems is key and using fresh, tested columns and bottled, tested eluents is essential. To judge the results, retention times must be the same and correct, peak areas must be the same and must match results acquired on installation and one should compare area ratios with installation result.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

We claim:

1. An automated sampling and reaction system comprising:
    an external sampling valve connected to a priming valve wherein the external sampling valve is configured to draw sample from a reactor or a reactor stream and the priming valve is configured to discharge wash to the external sampling valve, wherein the external sampling valve connects to the reactor or the reactor stream;
    a microreactor in fluidic communication with the external sampling valve and connected to a reagent valve, wherein the reagent valve is configured to discharge reagent to the microreactor and the external sampling valve is configured to discharge sample to the microreactor to form a secondary sample; and
    an injection valve connected to the microreactor and in fluidic communication with a column or detector, wherein the injection valve is configured to discharge the secondary sample into a solvent composition stream.

2. The automated sampling and reaction system of claim 1, further comprising a mixing tee connected to the external sampling valve and the microreactor.

3. The automated sampling and reaction system of claim 2, further comprising a diluent valve connected to the mixing tee, wherein the diluent valve is configured to discharge diluent to the mixing tee.

4. The automated sampling and reaction system of claim 1, further comprising a pumping system having one or more pumps working in combination with the priming valve and the reagent valve, wherein the priming valve is configured to draw wash from a wash reservoir or discharge wash to the external sampling valve and the reagent valve is configured to draw reagent from a reagent reservoir or to discharge reagent into the microreactor.

5. The automated sampling and reaction system of claim 3, further comprising a pumping system having one or more pumps working in combination with the priming valve, the diluent valve, and/or the reagent valve wherein the priming valve is configured to draw wash from a wash reservoir or discharge wash to the external sampling valve, the reagent valve is configured to draw reagent from a reagent reservoir or to discharge reagent into the microreactor, and the diluent valve is configured to draw diluent from the diluent reservoir and discharge diluent to the mixing tee.

6. The automated sampling and reaction system of claim 1, wherein in a first configuration, the external sampling valve draws a discrete amount of sample or continuous sample from a reactor or reactor flow stream and, in a second configuration, the external sampling valve discharges drawn sample via a backwash discharged from the sample pump to the mixing tee.

7. The automated sampling and reaction system of claim 3, wherein the diluent valve is configured to draw diluent from a diluent reservoir.

8. The automated sampling and reaction system of claim 1, wherein the system operates under a pressure greater than about 1 atmosphere.

9. The automated sampling and reaction system of claim 1, wherein the system is configured to draw from a non-pressurized source and further comprises at least one external auxiliary sampling valve and at least one external sample pump wherein the external auxiliary sample valve is connected to the external sample pump, the external sampling valve and to the reactor or reactor stream.

10. The automated sampling and reaction system of claim 9 wherein the system further comprises at least one selection valve connected to the external auxiliary sampling valve and to the external sampling valve.

11. The automated sample and reaction system of claim 1 wherein the system comprises a plurality of the external sampling valves and a selection valve connected to each of the external sampling valves.

12. The automated sample and reaction system of claim 1 wherein the microreactor is a chip, capillary, micro-structured or industrial type microreactor.

13. A liquid chromatography system comprising the automated sampling and reaction system of claim 1.

* * * * *

UNITED STATES PATENT AND TRADEMARK OFFICE
CERTIFICATE OF CORRECTION

PATENT NO. : 9,857,339 B2  
APPLICATION NO. : 14/979066  
DATED : January 2, 2018  
INVENTOR(S) : Hillary B. Hewitson et al.

Page 1 of 1

It is certified that error appears in the above-identified patent and that said Letters Patent is hereby corrected as shown below:

Column 1, Line 40:
- Replace the word "impurties" with the word "impurities".

Column 4, Line 67:
- Replace the word "ultraviolate" with the word "ultraviolet".

Column 5, Line 4:
- Replace the word "dischroism" with the word "dichroism".

Column 7, Line 1:
- Replace the word "spectroscopyisible" with the word "spectroscopy".

Column 10, Line 38:
- Replace the word "micoliters" with the word "microliters".

Column 21, Line 62:
- Replace the words "range between about about 10" with the words "range between about 10".

Column 22, Line 12:
- Replace "50 min–1 per reagent" with "50 min-1 per reagent".

Column 22, Line 14:
- Replace "50 milliliters (ml)–1 using 25 ml" with "50 milliliters (ml)-1 using 25ml".

Column 25, Line 24:
- Delete "scale of 10 s of seconds" and replace with "scale of 10s of seconds".

Column 26, Line 29:
- Delete "0.1 N acid" and replace with "0.1N acid".

Signed and Sealed this  
First Day of May, 2018

Andrei Iancu  
*Director of the United States Patent and Trademark Office*